United States Patent
Jiao et al.

(10) Patent No.: US 10,485,418 B2
(45) Date of Patent: Nov. 26, 2019

(54) FUNCTIONAL IMAGING OF PHOTORECEPTORS IN THE RETINA BY RHODOPSIN MAPPING

(71) Applicants: Shuliang Jiao, Miami, FL (US); Rong Wen, Coral Gables, FL (US); Byron L. Lam, Miami, FL (US); Tan Liu, Miami, FL (US)

(72) Inventors: Shuliang Jiao, Miami, FL (US); Rong Wen, Coral Gables, FL (US); Byron L. Lam, Miami, FL (US); Tan Liu, Miami, FL (US)

(73) Assignees: THE FLORIDA INTERNATIONAL UNIVERSITY BOARD OF TRUSTEES, Miami, FL (US); UNIVERSITY OF MIAMI, Miami, FL (US)

(*) Notice: Subject to any disclaimer, the term of this patent is extended or adjusted under 35 U.S.C. 154(b) by 284 days.

(21) Appl. No.: 14/816,812

(22) Filed: Aug. 3, 2015

(65) Prior Publication Data

US 2017/0035291 A1 Feb. 9, 2017

(51) Int. Cl.
| A61B 3/10 | (2006.01) |
| A61B 3/12 | (2006.01) |
| A61B 3/00 | (2006.01) |
| A61B 3/14 | (2006.01) |

(52) U.S. Cl.
CPC ............ *A61B 3/102* (2013.01); *A61B 3/0025* (2013.01); *A61B 3/12* (2013.01); *A61B 3/14* (2013.01)

(58) Field of Classification Search
None
See application file for complete search history.

(56) References Cited

U.S. PATENT DOCUMENTS

| 2011/0228223 A1* | 9/2011 | Jiao | A61B 3/102 351/206 |
| 2012/0188555 A1* | 7/2012 | Izatt | A61B 3/102 356/479 |
| 2016/0157715 A1* | 6/2016 | De Boer | A61B 3/0025 351/206 |

OTHER PUBLICATIONS

Van De Kraats, Jan et al. "The Pathways of Light Measured in Fundus Reflectometry," *Vision Res.*, 1996, 36(15):2229-2247.
Morgan, Jessica I.W. et al., "Scanning Laser Ophthalmoscope Measurement of Local Fundus Reflectance and Autofluorescence Changes Arising from Rhodopsin Bleaching and Regeneration," *Investigative Ophthalmology & Visual Science*, Mar. 2013, 54(3):2048-2059.

* cited by examiner

*Primary Examiner* — Darryl J Collins
*Assistant Examiner* — Journey F Sumlar
(74) *Attorney, Agent, or Firm* — Saliwanchik, Lloyd & Eisenschenk

(57) ABSTRACT

The subject invention provides novel apparatuses and methods for assessing the structure and function of photoreceptors in retina. In a specific embodiment, the assessment is accomplished by imaging rhodopsin, pigmented protein responsible for initiating vision acquisition of the eye, in living subjects. Advantageously, the technologies provided herein can be used for clinical evaluation of retinal photoreceptors for diagnosis, disease staging and follow-up, and outcome measurement for clinical trials of retinal degenerative disorders, including, for example, hereditary retinal degeneration and age-related macular degeneration.

15 Claims, 18 Drawing Sheets
(17 of 18 Drawing Sheet(s) Filed in Color)

FUNCTIONAL IMAGING OF PHOTORECEPTORS IN THE RETINA BY RHODOPSIN MAPPING

BACKGROUND

Photoreceptor cells in the retina are sensory neurons that convert light signals into neuronal signals via phototransduction, a process that initiates visual senses. Phototransduction occurs in photoreceptors in specialized organelles, the outer segments. Loss of photoreceptors can lead to vision loss. This is especially prevalent in patients with hereditary retinal degenerations such as retinitis pigmentosa (RP), which affects over 100,000 Americans. Mutations in close to 60 genes are responsible for RP. Loss of vision is not only a personal tragedy but also a burden to the society. It is estimated that an RP patient has an average health care cost of $7,000 annually.

Rhodopsin, the photosensitive molecule that absorbs photons and initiates phototransduction, is densely packed in the outer segments of rod photoreceptors. Rhodopsin has intrinsic absorbance in the visible spectrum in the dark adapted state. When exposed to light, the absorption spectrum of rhodopsin undergoes a dramatic shift. Thus, rhodopsin is a functional biomarker for rod photoreceptors and, by imaging rhodopsin, the function of photoreceptors can be assessed.

The light-induced shift in rhodopsin absorption spectrum has been explored to assess the concentration of rhodopsin, thus of photoreceptors, in vivo. Fundus reflection densitometry, which measures the difference in rhodopsin light absorption in the dark- and light-adapted states, was developed to quantitatively assess rhodopsin in the retina. The first experimental setup based on fundus reflectometry was developed in the 1950s and was improved thereafter.

Early imaging techniques for fundus densitometry used fundus photographs on film, and later used, for example, video-based fundus reflectometers, scanning laser ophthalmoscopes (SLO), and charged-couple device (CCD) based fundus cameras. Currently, optical coherence tomography (OCT), SLO, and fundus photography are the major imaging techniques used for imaging the retinal structures. To date, however, little progress has been made in assessing quantitatively, via means of optical imaging, the function and structure of photoreceptors in vivo, which could provide crucial information for the diagnosis and monitoring of retinal degenerative disorders.

BRIEF SUMMARY

The subject invention provides novel apparatuses and methods for assessing the structure and function of photoreceptors in a retina. In a specific embodiment, the assessment is accomplished by imaging rhodopsin, which is the pigmented protein responsible for initiating vision acquisition of the eye. Advantageously, the technologies provided herein can be used for clinical evaluation of retinal photoreceptors for diagnosis, disease staging and follow-up, and outcome measurement for clinical trials relating to retinal degenerative disorders, including, for example, hereditary retinal degeneration and age-related macular degeneration.

In one aspect, the subject invention provides an apparatus for evaluating the function of the retina of a subject based on an optical coherence tomography (OCT) technology, comprising a first source providing light with near-infrared (NIR) wavelengths and a second source providing light with visible (VIS) wavelengths sufficient to activate optical absorption of photosensitive molecules of the retina.

The subject can be a human or a non-human mammal such as, for example, a mouse, rat, dog, rabbit, cat, or non-human primate. In a preferred embodiment, the subject is a human.

In a specific embodiment, the photosensitive molecules are rhodopsin. Because rhodopsin undergoes a shift in its absorption spectrum at a wavelength of about 500 nm, embodiments of the subject invention provide an apparatus capable of emitting visible light, in addition to near-infrared light.

In some embodiments, the OCT apparatus is integrated with a scanning laser ophthalmoscope (SLO) capable of performing retinal fundus imaging with a laser source.

In some embodiments, the SLO comprises a plurality of parallel optical fibers by which the incident laser source is split, the optical fibers illuminating pulsed laser spots onto the sample retina. Advantageously, the scanning speed of the SLO increases by a multiplication factor equivalent to the number of parallel optical fibers provided.

In some embodiments, the time delay between adjacent laser pulses is controlled by the difference in lengths between the optical fibers from which the pulses originate. Exemplary embodiments provide that the time delay between adjacent pulses is less than about 1 µs, and preferably between about 1 ns and about 10 ns. The time delay among pulses allows the detection of the reflection of these pulses from the retina with a single detector, e.g., a photomultiplier tube (PMT).

In certain embodiments, the OCT apparatus further comprises means of separating the VIS light source into a plurality of wavelength bands in accordance with the plurality of distinct optical absorption coefficients characteristic to rhodopsin. In an exemplary embodiment, the VIS light source is split into three distinct wavelength bands corresponding to three distinct optical absorption coefficients characteristic to rhodopsin. Non-limiting examples of the means of separating the VIS light include the use of three distinct band-pass filters and the use of a single, three-band filter.

In another aspect, the subject invention provides a method of examining the function of the retina of a human, comprising:

collecting three-dimensional images of the retina in a dark environment and in a bright environment, respectively, using an optical coherence tomography (OCT) apparatus equipped with a near-infrared (NIR) light source and a visible (VIS) light source;

quantifying the optical absorption of the retina in the dark and the bright environment, respectively, based on the intensity of the OCT images collected under each condition;

using an appropriate model of fundus reflection to correlate the difference in intensity of the images captured in the dark and the bright environment, respectively, with the optical density of rhodopsin present in the retina; and providing an assessment of the function of the retina based on the optical density of rhodopsin.

In some embodiments, the method of using the OCT apparatus to collect three-dimensional retinal images comprises:

allowing the subject to adapt to a dark environment;

capturing a retinal image with the NIR light source in the dark environment;

optimizing each imaging parameter with the NIR light source in the dark environment;

capturing a first series of cross-sectional images with the VIS light source in the dark environment;

allowing the subject to adapt to a bright environment;
capturing a second series of cross-sectional images with the VIS light source in the bright environment;
summing the signal intensities of the cross-sectional images along the axial direction by which the images are collected in the dark and the bright environment, respectively; and reconstructing a three-dimensional image of the retina for the dark- and the light-adapted environment, respectively.

In a specific embodiment, the wavelength of the VIS light source is sufficient to activate the optical absorption of rhodopsin.

Embodiments of the subject invention provide that the reconstructed three-dimensional retinal image comprises the spatial distribution of the rhodopsin whose optical absorption is quantified by the intensity of the image.

In yet another aspect, the subject invention provides an apparatus for retinal fundus imaging based on a scanning laser ophthalmoscopy (SLO) technology, comprising a laser source split by a plurality of parallel optic fibers, the optical fibers illuminating pulsed laser spots onto the sample retina. Advantageously, the scanning speed of the SLO increases by a multiplication factor equivalent to the number of parallel optical fibers provided.

In some embodiments, the time delay between adjacent laser pulses is controlled by the difference in lengths between the optical fibers from which the pulses originate. Exemplary embodiments provide that the time delay between adjacent pulses is less than about 1 µs, and preferably between about 1 ns and about 10 ns. The time delay among pulses allows the detection of the reflection of these pulses from the retina with a single detector, e.g., a PMT.

Advantageously, the imaging technologies disclosed herein are capable of providing quantitative assessment of the structure and function of retinal photoreceptors in vivo. Specifically, apparatuses and methods are provided to measure the concentration and distribution of rhodopsin in living subjects.

BRIEF DESCRIPTION OF THE DRAWINGS

The patent or application file contains at least one drawing executed in color. Copies of this patent or patent application publication with color drawings will be provided by the Patent Office upon request and payment of the necessary fee.

FIG. 4A is a dark-adapted image. FIG. 4B is a first light-adapted image. FIG. 4C is a second light-adapted image acquired immediately after FIG. 4B. FIG. 4D is a differential image calculated between FIGS. 4A and 4B using Equation 2. FIG. 4E is a differential image between FIGS. 4B and 4C calculated using Equation 2. FIGS. 4A-4C share the same color map, while FIGS. 4D and 4E share the same color map. Scale bar=500 µm.

FIGS. 5A-5C represent summation of OCT signals from all imaging depths. FIG. 5A is a dark-adapted image. FIG. 5B is a light-adapted image. FIG. 5C is the differential image of FIGS. 5A and 5B. FIGS. 5D-5E represent signals from the inner segment/outer segment and the retinal pigment epithelium (RPE) only. FIG. 5D is a dark-adapted image. FIG. 5E is a light-adapted image. FIG. 5F is the differential image of FIGS. 5D and 5E. FIGS. 5A, 5B, 5D, and 5E share the same color map, while FIGS. 5C and 5F share the same color map. Scale bar=500 µm.

FIG. 6A is the averaged cross-sectional image from all the B-scans of the dataset of the dark-adapted retina shown in FIG. 4A. FIG. 6B is the averaged cross-sectional image from all the B-scans of the dataset of the light-adapted retina shown in FIG. 4B. FIG. 6C is the differential image of FIGS. 6A and 6B calculated using Equation 2. FIG. 6D shows the averaged A-scans from the light-to-dark transition, represented by the blue line, and the light-to-light transition, represented by the red line of the differential images for the albino rat. FIG. 6E is the averaged cross-sectional differential image calculated between the dark- and the light-adapted states of a pigmented rat retina using Equation 2. FIG. 6F is the averaged A-scans from A-scans from the light-to-dark transition, represented by the blue line, and the light-to-light transition, represented by the red line of the differential images for the pigmented rat.

FIG. 7A is an en-face view of the OCT dataset of the dark-adapted retina where the vertical strip marked with the dotted yellow lines had been bleached with a laser having a wavelength of 532 nm. FIG. 7B is an en-face view of the OCT dataset of the light-adapted retina. FIG. 7C is the differential image between FIGS. 7A and 7B calculated using the same method as for FIG. 4C. FIG. 7D is the averaged cross-sectional image of the same dark-adapted retina as in FIG. 7A. FIG. 7E is the averaged cross-sectional image of the same light adapted retina as FIG. 7B. FIG. 7F is the differential image between FIGS. 7D and 7E calculated using the same method as for FIG. 6C. Scale bar=100 µm.

FIG. 8A exemplifies the 8-channel design that splits a single laser source into 8 beams by a series of single-mode fiber couplers. FIG. 8B represents the x and y mirrors of a galvanometer scanner and the configuration thereof. Further, FIG. 8B demonstrates the configuration of the light spots projected onto the scanner mirrors. FIG. 8C illustrates the overall configuration of the SLO apparatus.

FIG. 11A shows both the NIR and the VIS OCT light sources integrated with a 4-channel SLO light source. FIG. 11B represents the x and y mirrors of a galvanometer scanner and the configuration thereof. Further, FIG. 11B demonstrates the configuration of both the OCT and the SLO light spots projected onto the scanner mirrors. FIG. 11C illustrates the overall configuration of the integrated OCT-SLO apparatus.

FIG. 12A shows the first design with three distinct band-pass filters. FIG. 12B shows the second design with a single band-pass filter.

DETAILED DESCRIPTION

Figure 1:
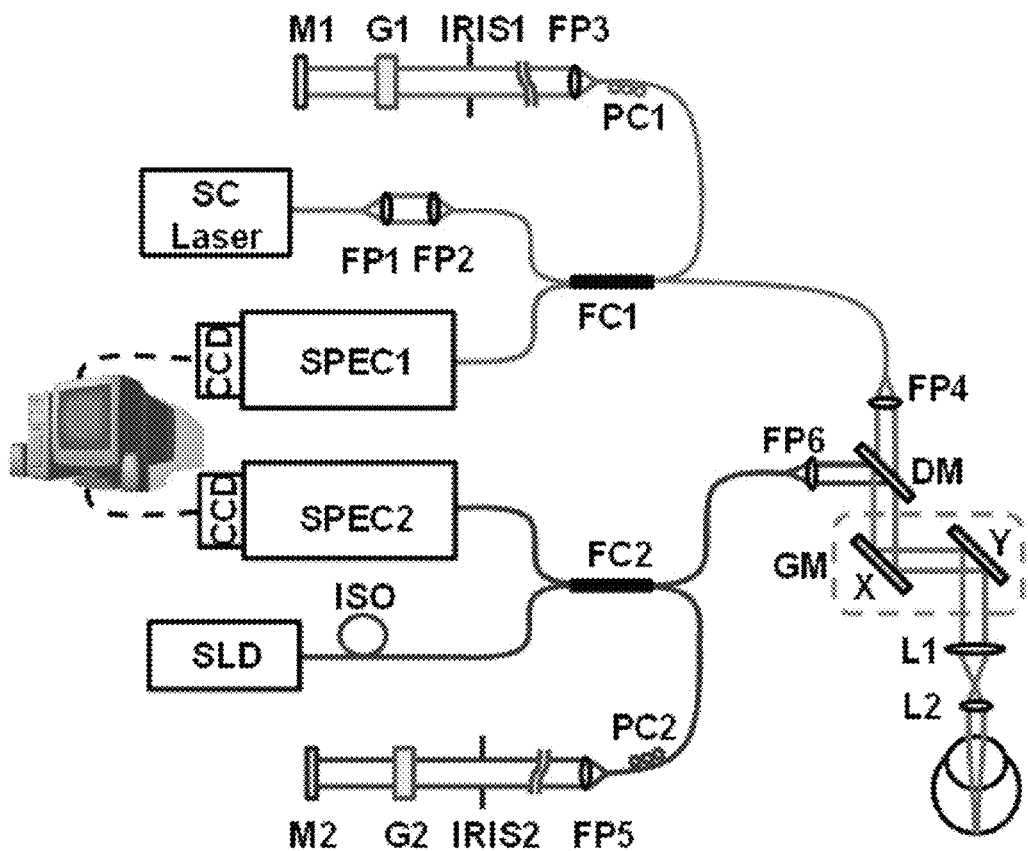
FIG. 1 is a schematic of the NIR/VIS-OCT imaging apparatus.

In the following detailed description, reference is made to the accompanying drawings, depicting exemplary, non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims.

The subject invention provides novel apparatuses and methods for assessing the structure and function of photoreceptors in a retina. In a specific embodiment, the assessment is accomplished by imaging rhodopsin, the pigmented protein responsible for initiating the process of vision acquisition. Advantageously, the technologies provided herein can be used for clinical evaluation of retinal photoreceptors for diagnosis, disease staging and follow-up, and outcome measurement for clinical trials relating to retinal degenerative disorders, including, for example, hereditary retinal degeneration and age-related macular degeneration.

In one aspect, the subject invention provides an apparatus for evaluating the function of the retina of a living subject based on an optical coherence tomography (OCT) technology, comprising a first source providing light with near-infrared (NIR) wavelengths and a second source providing light with visible (VIS) wavelengths sufficient to activate optical absorption of photosensitive molecules of the retina. In a specific embodiment, the OCT apparatus provided herein is a spectral-domain OCT apparatus.

OCT is a well-known imaging technique in biomedicine capable of optical sectioning of semi-transparent tissues. OCT, which is based on low-coherence interferometry, is applied in ophthalmology because of its great power in noninvasive retinal and macular imaging. A major advantage of OCT over other imaging techniques is its ability to simultaneously measure a sample's quantitative 3D surface topography and internal 3D volumetric data.

One individual OCT depth scan is referred to as an A-scan, which can be treated as an integral over depth dependent reflectivity of the object under measurement. The most common OCT imaging method is B-scan imaging, where several A-scans are combined together to form a cross-sectional image of the object structure called a tomogram. In addition to cross-sectional imaging, OCT is capable of revealing the whole 3D structure of the sample by volume reconstruction.

Conventionally, an OCT apparatus comprises a source providing light with near-infrared wavelengths, vertical and horizontal scanning elements, a set of lenses to focus the NIR light onto the sample retina, and a series of filters, detectors to collect reflected light signals, and data processors. The subject invention provides a modified OCT apparatus that, in addition to these standard elements, is equipped with an additional visible light source.

The modified OCT of the subject invention employs two distinct light sources operating at different wavelengths to accomplish both structural and functional assessment of rhodopsin. In an exemplary embodiment, the NIR light source operates at center wavelength of about 840 nm, and the VIS light source operates at a center wavelength of about 520 nm. The NIR- and VIS-OCT probe light beams are coaxial and delivered to the eye by the same scanning and imaging optics to ensure that they image the same retinal area of interest. The NIR light source is used to perform the initial alignment for imaging the retinal area of interest before imaging the rhodopsin with the VIS light source. Devices providing the light sources can be, for example, a superluminescent diode (SLD) or a supercontinuum laser. However, persons with ordinary skill in the art will recognize that other suitable devices capable of providing broadband light to an OCT apparatus, now known or hereafter developed, may also be used.

The subject can be a human or a non-human mammal, such as, for example, a mouse, rat, dog, rabbit, cat, or non-human primate. In a preferred embodiment, the subject is a human.

In a specific embodiment, the photosensitive molecules are rhodopsin. Rhodopsin has intrinsic absorbance in the visible spectrum in a dark-adapted state. After absorbing a photon, a rhodopsin molecule undergoes conformational changes with a dramatic shift in its absorption peak ($\lambda_{peak}$) from about 500 nm to about 380 nm, rendering it a functional biomarker for photoreceptors, and thus the retina. This light-induced shift, generated by a process known as photobleaching, or bleaching for short, has been used to assess rhodopsin content by retinal densitometry or optical reflectometry. Advantageously, the subject invention combines the depth-resolving capability of conventional OCT with quantification of rhodopsin's optical absorption by visible light excitation to provide an assessment of both the distribution and function of photoreceptor in the retina.

In an exemplary embodiment, the VIS-OCT operates at a center wavelength of about 520 nm with a bandwidth of about 8.8 nm, sufficient to resolve all the cell layers of the retina.

In some embodiments, the OCT apparatus is integrated with a scanning laser ophthalmoscope (SLO) capable of performing retinal fundus imaging with a laser source.

The ophthalmoscope is well known as an important device for examining the eye, and in particular the retina. A precise correlation between retinal anatomy and retinal functioning can be established with the SLO. This retinal function mapping is now known to be very helpful to the surgeon when applying therapeutic laser treatment.

A conventional SLO comprises directing a narrow laser beam via a mirror system onto the eye fundus. The light reflected from the fundus is directed to a detector that produces an electrical output proportional to the intensity of the detected light. The electrical output can then be recorded or displayed on a visual display unit. By moving the mirror system according to a scanning sequence in a raster fashion and synchronizing the detector to the scanning sequence, it is possible to produce an image of the fundus.

In some embodiments, the SLO provided herein comprises a plurality of parallel optical fibers by which the incident laser source is split, the optical fibers illuminating pulsed laser spots onto the sample retina.

The novel design of a plurality of parallel optical fibers splitting the incident laser source addresses two technical issues that render the current SLO technologies or fundus camera based reflectometers inaccurate. The two issues are the scanning speed of the SLO and the influence of absorption by rhodopsin intermediates.

The accuracy of fundus reflection imaging depends highly on the sensitivity of the imaging system, the theoretical model of ocular reflection used for calculating optical density of visual pigments, and the imaging speed. Fundus cameras can image the retina with a snapshot, which alleviates the effect of eye motion; however, the imaging qualities are susceptible to stray light, which affects the dynamic range and signal-to-noise ratio (SNR). Confocal SLO has the advantage of higher dynamic range and better SNR; however, as a point-scanning imaging technology, SLO-based fundus reflectometry is more sensitive to eye motion. An increase in imaging speed can improve the performance of SLO-based fundus densitometer. In specific embodiments of the subject invention the imaging speed of the SLO is adjustable and can increase by a multiplication factor equivalent to the number of parallel optical fibers provided, reducing the effect of eye movement on the quality of the image.

In some embodiments, the time delay between adjacent laser pulses as provided by the plurality of optical fibers is controlled by the difference in lengths between the optical fibers from which the pulses originate. In preferred embodiments, the time delay between pulses can be reduced to be less than about 1 µs, with exemplary embodiments yielding a delay between about 1 ns and about 10 ns. The time delay among pulses allows the detection of the reflection of these pulses from the retina with a single detector, e.g., a PMT. Advantageously, shortened laser pulses can minimize the effects of light absorption by rhodopsin intermediates contributing to the overall quantification of rhodopsin absorption.

When activated by light, rhodopsin undergoes various intermediate stages before becoming fully bleached in a process known as the rhodopsin photocycle. The rhodopsin intermediates generated during the photocycle also absorb the probing light, resulting in absorption spectra overlapped with the original rhodopsin absorption, a process typically not accounted for by many previous fundus reflectometry studies. The probing light of technologies based on either a fundus camera or conventional SLO systems is in the microsecond range, long enough to include the absorption of all the rhodopsin intermediates, leading to an overestimation of rhodopsin content in the retina. Although absorption by the intermediates cannot be avoided, it can be minimized by shortening the duration of the probing light to the nanosecond (ns) range.

Another advantage of the nanosecond pulse illumination is that the imaging speed and the exposure time for each imaging spot are decoupled. Thus, the exposure time is determined by the pulse duration while the imaging speed is determined by the pulse repetition rate (PRR).

In an exemplary embodiment, the integrated OCT-SLO system of the subject invention can be used to examine the absorption of rhodopsin in both dark and bright environments, providing both three-dimensional and topographical assessment of the concentration of rhodopsin in the retina. The method of using the integrated apparatus is exemplified by the following steps. In the dark environment, only the SLO is in operation in order to avoid the generation of rhodopsin intermediates by the VIS-OCT's probing light. In the bright environment, the VIS-OCT data are obtained simultaneously with the SLO data, such that the VIS-OCT scan density would be ¼ of that of the SLO. The VIS-OCT data of a dark-adapted retina can be obtained by, for example, rescanning the retina with the VIS-OCT, with the SLO switched off, to cover the missing area of interest immediately after the SLO scan is completed.

In certain embodiments, the OCT apparatus can further comprise a means of separating the VIS light source into a plurality of wavelengths in accordance with the plurality of distinct optical absorption coefficients characteristic to rhodopsin. Spectral separations of the absorption bands are necessary to avoid bleaching of rhodopsin by photons not used for image quantification. In an exemplary embodiment, the light exposure is kept at levels such that less than 10% of the rhodopsin is bleached by the OCT scan. At these low levels, the concentration of rhodopsin can be treated as constant during the exposure time of the camera.

In an exemplary embodiment, the VIS light source can be split into three distinct wavelength bands corresponding to the three distinct optical absorption coefficients characteristic to rhodopsin. These distinct absorption coefficients correspond to absorption bands having center wavelengths at about 520 nm, about 550 nm, and about 580 nm, respectively, with 520 nm being the closest to the $\lambda_{peak}$ of rhodopsin.

Preferred means of separating the VIS light include the use of three distinct band-pass filters and the use of a single filter capable of separating the source light into three distinct wavelengths. For the first means, the source light is initially split by a 1×3 single-mode optical fiber coupler, collimated, and then passed through three band-pass filters with center wavelengths set at, for example, about 520 nm, 550 nm, and 580 nm, respectively. Further, the three bands, having the same full width at half-maximum (FWHM) values, are coupled into a 3×1 fiber combiner to become a single beam, which undergoes further splitting in the source arm before illuminating the sample. In contrast, the second means combines the splitting and filtering of the source light into one single filter, followed by further splitting in the source arm. Persons with ordinary skills in the art will recognize that other means of separating a light source into bands of different wavelengths, now known or hereafter developed, may also be used.

In another aspect, the subject invention provides a method of examining the function of the retina of a human, comprising:
    collecting three-dimensional images of the retina in a dark and a bright environment, respectively, using an optical coherence tomography (OCT) apparatus equipped with a near-infrared (NIR) light source and a visible (VIS) light source;
quantifying the optical absorption of the retina in the dark and the bright environment, respectively, based on the intensity of the OCT images collected under each condition;
using an appropriate model of fundus reflection to correlate the difference in intensity of the images captured in the dark and the bright environment, respectively, with the optical density of rhodopsin present in the retina; and
providing an assessment of the function of the retina based on the optical density of rhodopsin.

In some embodiments, the method of using the OCT apparatus to collect three-dimensional retinal images comprises:
    allowing the subject to adapt to a dark environment;

capturing a retinal image with the NIR light source in the dark environment;
optimizing each imaging parameter with the NIR light source in the dark environment;
capturing a first series of cross-sectional images with the VIS light source in the dark environment;
allowing the subject to adapt to a bright environment;
capturing a second series of cross-sectional images with the VIS light source in the bright environment;
summing the signal intensities of the cross-sectional images along the axial direction by which the images are collected in the dark and the bright environment, respectively; and
reconstructing a three-dimensional image of the retina for the dark- and the light-adapted environment, respectively.

The OCT apparatus equipped with both an NIR and a VIS light source provides three-dimensional depth information of the optical absorption of rhodopsin in different layers of the ocular media, including, for example, the ocular media anterior to the photoreceptor layer where wave guiding begins, the photoreceptor layer where reflection by the discs and absorption by visual pigments such as the rhodopsin occurs, and the post-photoreceptor layer (Morgan, J. I. & Pugh, E. N. Scanning laser ophthalmoscope measurement of local fundus reflectance and autofluorescence changes arising from rhodopsin bleaching and regeneration. *Invest ophthalmol & Vis Sci.* 54, 2048-59 (2013)). The post-photoreceptor layer further comprises the retinal pigment epithelium, the choroid, and the sclera. To quantify the concentration and distribution of rhodopsin, OCT absorption data can be applied to a fundus reflection mathematical model expressed as follows (van de Kraats, J., Berendschot T. T. & van Norren, D. The pathways of light measured in fundus reflectometry. *Vision Res.* 36, 2229-2247 (1996)):

$$R_{eye}(\lambda)=T_\lambda^2\{R_{prePRL}+[1-R_{prePRL}]^2[R_{PRL}(\lambda)+R_{postPRL}(\lambda)]\} \quad [1]$$

where $T_\lambda$ is the transmissivity of the ocular media anterior to the photoreceptor layer, $R_{prePRL}$ is the reflectance of the ocular media anterior to the photoreceptor layer, $R_{PRL}$ is the reflectance of the photoreceptor layer, and $R_{postPRL}$ is the reflection from the post-photoreceptor layer. Photobleaching only affects the value of $R_{PRL}$, while values of $R_{prePRL}$ and $R_{postPRL}$ remain constant before and after photo-bleaching.

Embodiments of the subject invention provide that two OCT images form the same retinal area, the first captured in the dark environment and the second captured in the bright environment, are used to complete the assessment.

The VIS-OCT first takes a full 3D dataset comprising a series of B-scans of a dark-adapted retina, guided by the NIR-OCT. In certain embodiments, the operator of the OCT can be in a separate room from the patient or remain in the same dark room and use a virtual reality system with a displaying goggle that serves as a computer monitor to avoid excessive light exposure. After imaging the dark-adapted retina, the patient is allowed to stay in a well-lit room for light adaptation in order to completely bleach rhodopsin, which is followed by imaging the light-adapted retina with the VIS-OCT.

The intensity of the OCT images, indicative of rhodopsin absorption in their respective state, are processed using the following equation:

$$I_R(x, y) = \frac{I_{light}(x, y) - I_{dark}(x, y)}{I_{light}(x, y)} \quad [2]$$

where $I_{light}$ and $I_{dark}$ represent image intensity of the retina in the light- and dark-adapted state, respectively, while x and y represent the coordinates of each image. The value of $I_R$ is then averaged across all A-scans after aligning the images with respect to the inner segments (IS) and the outer segments (OS) of the photoreceptors in the direction in which the images are taken.

Exemplary data based on depth-resolved fundus reflection suggest that rhodopsin absorption affects the light signals reflected from both the photoreceptor and the post-photoreceptor layers, allowing Equation 1 to be simplified to:

$$R_{eye}(\lambda)=T_\lambda^2\{R_{prePRL}+[1-R_{prePRL}]^2 R_{PRL}(\lambda)\} \quad [3]$$

where $R_{PRL}$ represents the reflectance of photons interacted with the photoreceptor layer, including those reflected by the OS of the photoreceptors and those reflected by the post-photoreceptor layer.

For the light-adapted state, the VIS-OCT images are segmented at the photoreceptor layer. By summing the OCT signals anterior and posterior to the photoreceptor layer and by equalizing the total reflections of the OCT signals at corresponding locations, $T_\lambda^2 R_{prePRL}$ and $T_\lambda^2 [1-R_{prePRL}]^2 R_{PRL}(\lambda)$ of Equation 3 are obtained. Equation 4 can be subsequently rewritten to be based on intensities of the dark- and the light-adapted images for a given wavelength $\lambda$:

$$\frac{R_{eye-l}(\lambda) - R_{eye-d}(\lambda)}{T_\lambda^2[1-R_{prePRL}]^2 R_{PRL-l}(\lambda)} = \frac{R_{PRL-l}(\lambda) - R_{PRL-d}(\lambda)}{R_{PRL-l}(\lambda)} = \exp(-2D_{Rho}) \quad [4]$$

where $R_{eye-d}$ and $R_{eye-l}$ are the dark- and light-adapted fundus reflections, respectively, and $D_{Rho}$ is the optical density of rhodopsin in rod photoreceptors. $D_{Rho}$ can be expressed as the product of its extinction coefficient ($\alpha_\lambda$), the length (l) of the light path in the OS, and the concentration of rhodopsin ($C_D$) in the OS, related by the following equation:

$$D_{Rho}=\alpha_\lambda l C_D \quad [5].$$

In a specific embodiment, the wavelength of the VIS light source is sufficient to activate the optical absorption of the rhodopsin. Preferably, the wavelength is centered at about 520 nm.

The VIS-OCT technology for rhodopsin imaging can be used to evaluate quantitative topographic distribution of rhodopsin and thus the functional rod photoreceptors in the retina. As a functional biomarker for rod photoreceptor metabolism and survival, rhodopsin OCT is of value in the diagnosis, longitudinal monitoring of disease progression, and efficacy evaluation of treatments in a variety of retinal disorders including retinal degenerations, inflammatory retinopathies, and vascular retinal disorders. For example, this technology can be used for clinical care and evaluation of treatments in patients with hereditary retinal degenerations such as retinitis pigmentosa (RP), a group of genetically heterogeneous photoreceptor degenerative disorders with the prevalence of 1 in 3,000-4,500 people.

Rhodopsin OCT can also be used in the early diagnosis of age-related macular degeneration (AMD) in which degeneration of rod photoreceptors exceeds the loss of cone photoreceptors.

Furthermore, the technology disclosed herein also provides an important anatomically functional measure in the assessment of regenerative therapeutics including, but not limited to, stem cell, gene therapy, and neuroprotective agents.

In yet another aspect, the subject invention provides an apparatus for retinal fundus imaging based on a scanning laser ophthalmoscopy (SLO) technology, comprising a laser source split by a plurality of parallel optic fibers, the optical fibers illuminating pulsed laser spots onto the sample retina. Advantageously, the scanning speed of the SLO increases by a multiplication factor equivalent to the number of parallel optical fibers provided.

In some embodiments, the time delay between adjacent laser pulses is controlled by the difference in lengths between the optical fibers from which the pulses originate. Exemplary embodiments provide that the time delay between adjacent pulses is less than about 1 µs, and preferably between about 1 ns and about 10 ns. The time delay among pulses allows the detection of the reflection of these pulses from the retina with a single detector, e.g., a PMT.

The subject invention further provides a method comprising the use of a scanning laser ophthalmoscope (SLO) integrated with the OCT apparatus, wherein, by utilizing a combination of the VIS-OCT and the SLO images, a quantification of the rhodopsin concentration is achieved such that the VIS-OCT image provides absorption information along a depth. In a further embodiment, quantitative rhodopsin distribution is calculated from three VIS-OCT images of dark-adapted retina simultaneously acquired.

Advantageously, the imaging technologies disclosed herein are capable of providing qualitative and quantitative assessment of the structure and function of retinal photoreceptors in vivo. Specifically, apparatuses and methods are provided to measure the concentration and distribution of rhodopsin in living subjects.

EXAMPLES

Following are examples which illustrate procedures for practicing the invention. These examples should not be construed as limiting.

Example 1

A schematic of the NIR/VIS-OCT imaging system is shown in FIG. 1. The system comprises two independent spectral domain-OCT subsystems, one of which is equipped with a near-infrared (NIR) light source for guiding the image alignment process in a dark environment and the other is equipped with a visible (VIS) light source for rhodopsin imaging.

The VIS-OCT employs a supercontinuum laser source (EXB-6, SuperK EXTREME, NKT Photonics, Denmark) equipped with a variable band-pass filter (SuperK Varia, NKT Photonics). The filtered light output (center wavelength: 520 nm, bandwidth: 9.3 nm, 80 MHz pulse rate) is delivered though a fiber delivery module. The VIS light is coupled into the source arm of a single-mode optical fiber-based Michelson interferometer by using a pair of identical fiber ports (PAF-X-11-A, Thorlabs). The NIR-OCT employs a superluminescent diode (SLD-37-HP, center wavelength: 840 nm, bandwidth: 50 nm, Superlum, Russia). The NIR- and VIS-OCT probe light beams are coaxial and delivered to the eye by the same scanning and imaging optics to ensure that they image the same area of the retina.

After passing through an optical fiber isolator, the NIR light is coupled into another single-mode fiber-based Michelson interferometer. After exiting their corresponding optical fibers in the sample arms, the VIS and NIR light beams are collimated and combined by a dichroic mirror. The combined light beam is scanned by a x-y galvanometer (6215H, Cambridge) scanner, and then delivered into the eye by the combination of a relay lens (f=75 mm) and a 60D Volk lens. The VIS light power is 240 µW before entering the eye, and the NIR light at the same location is 600 µW. The theoretical axial resolution of the VIS-OCT is 12.5 µm in air and 13.7 µm in the eye.

In the detection arm of each OCT subsystem the reflected light from the sample and reference arms is collimated and detected by a spectrometer. The VIS-OCT spectrometer comprises an 1800 line/mm transmission grating, a multi-element imaging lens (f=150 mm), and a line scan charge-coupled device (CCD) camera (Sprint spL2048-70k, 2048 pixels with 10 µm pixel size; Basler, Ahrensburg, Germany). The NIR-OCT uses a spectrometer with the same parameters detailed in a previous publication (Dai, C., Liu, X., Zhang, H. F., Puliafito, C. A. & Jiao, S. Absolute retinal blood flow measurement with a dual-beam Doppler optical coherence tomography. *Invest Ophthalmol Vis Sci.* 54, 7998-8003 (2013)). Two image acquisition boards (NI IMAQ PCIe-1433 for VIS-OCT and PCIe-1429 for NIR-OCT) acquire interference spectra captured by the cameras and subsequently stream the spectra to a computer workstation for data processing. Spectrometer sensitivity fall-off over imaging depth is measured and compensated before data analysis. The exposure time of the camera of the VIS-OCT is set to about 11 µs. The camera is synchronized by the sampling clock of an analogue output board (PCI-6731, National Instruments) whose output controls the operation of the galvanometer scanner. The A-scan rate is set to 64 kHz.

Figure 2A:
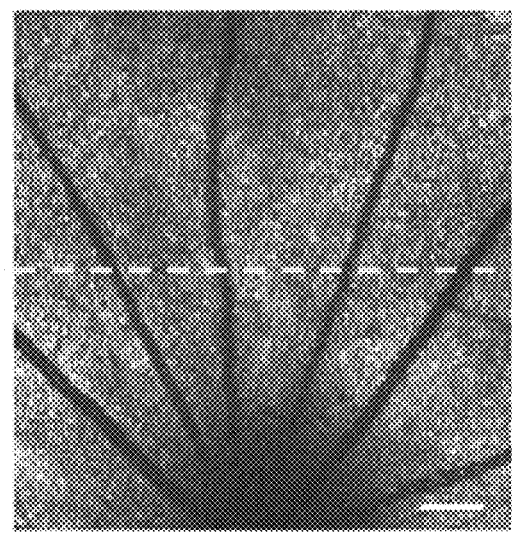
FIG. 2A is a VIS-OCT fundus image of a rat retina generated by projecting the 3D OCT data onto the x-y plane.
Figure 2B:
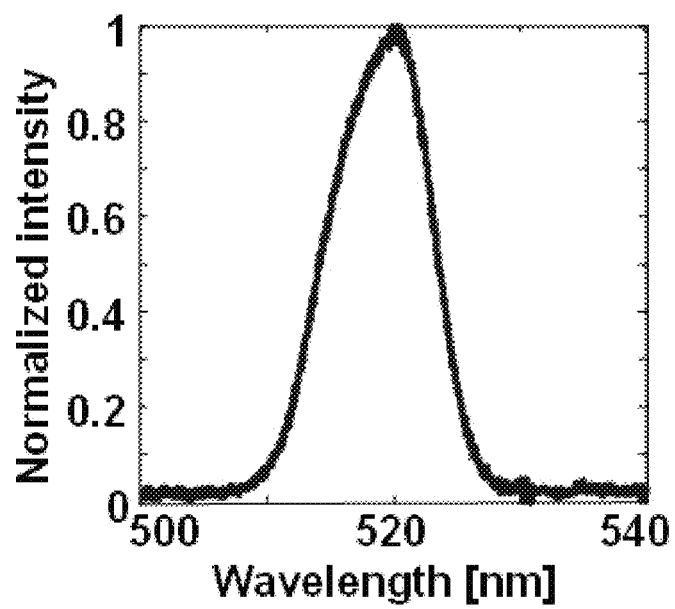
FIG. 2B shows a spectrum of the light source of the VIS-OCT apparatus.
Figure 3A:
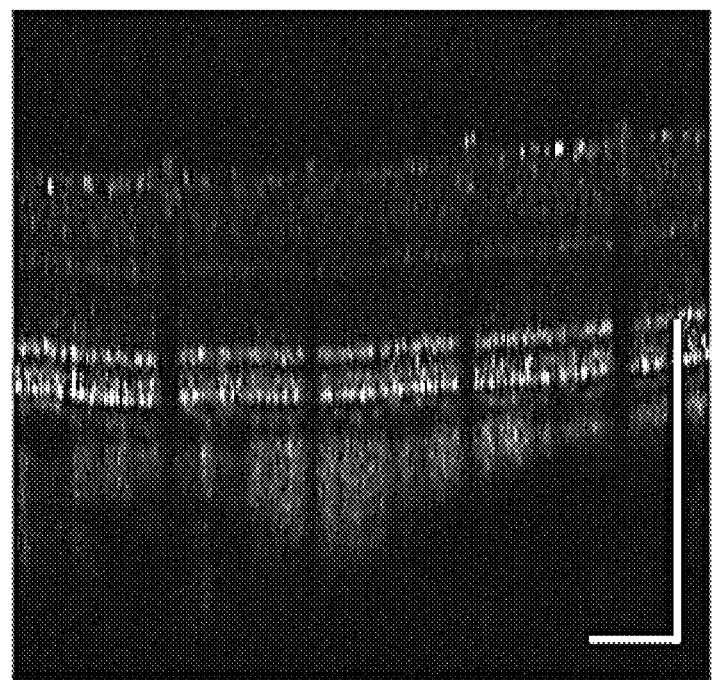
FIG. 3A is a VIS-OCT cross-sectional image consisting of 2048(x)×1265(y) pixels displayed in a linear scale at the location marked as a dotted line on FIG. 2A.
Figure 3B:
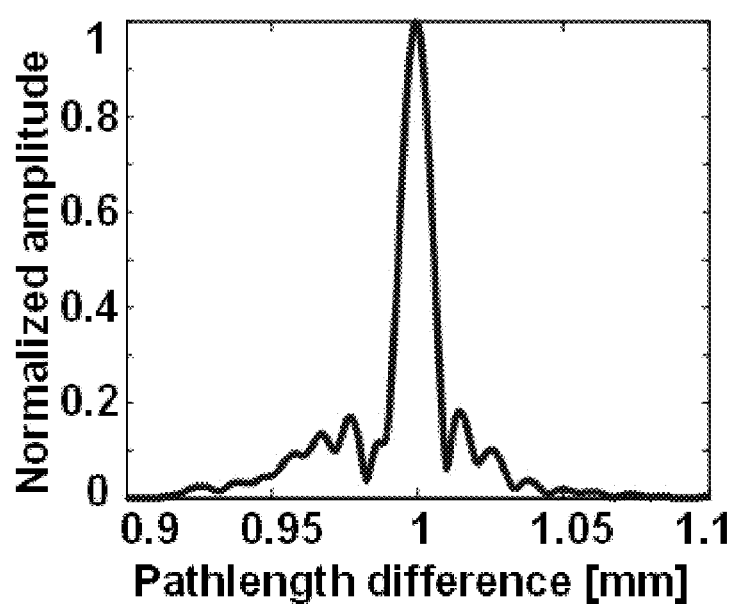
FIG. 3B is the measured point spread function (PSF) of the VIS-OCT.

The performance of the VIS-OCT system can be demonstrated by a 3D dataset of a rat retina represented either in a projected OCT fundus image (FIG. 2A) or a cross-sectional image (B-scan, FIG. 3A). All the major retinal layers can be recognized in the cross-sectional image.

Example 2

Two animal models were used for imaging rhodopsin with the NIR/VIS-OCT. The first model comprised albino rats with normal retina (Sprague Dawley, 200-400 g, Harlan Laboratories), and the second model comprised wild-type pigmented rats (Long Evans, 200-400 g, Harlan Laboratories).

The rats were dark-adapted for about 4 hours prior to each experiment (Behn, D. et al. Dark adaptation was faster in pigmented than albino rats. *Doc Ophthalmol.* 106, 153-159 (2003)). A cocktail containing ketamine (54 mg/kg body weight) and xylazine (6 mg/kg of body weight) was intraperitoneally injected for anesthesia. The rat's pupil was dilated with 0.5% tropicamide ophthalmic solution and 0.5% proparacaine hydrochloride ophthalmic solution. After the rats were sedated, a powerless contact lens was put on the eye to prevent cornea dehydration and cataract formation (Liu, X. et al. Effect of contact lens on optical coherence tomography imaging of rodent retina. *Curr Eye Res.* 38, 1235-1240 (2013)).

In the rhodopsin imaging experiments, a raster scanning pattern was set to cover a 39°×39° area of the rat retina. In the patterned bleaching experiment, a continuous-wave (CW) laser bleached an area covering 7.8°×19.5° in dark-adapted state 15 seconds before the OCT-scan was acquired. The OCT scans of the dark- and light-adapted states for the pattern bleach experiment covered an area of 39°×19.5°.

Example 3

The following example pertains to imaging rhodopsin using an albino rat. The VIS source had a center wavelength of about 530 nm and a bandwidth of about 9.3, enabling a depth resolution of about 13 μm in air. The NIR source operated at a center wavelength of about 840 nm. Following dark-adaptation for about 4 hours, the retinal area of interest was located and the retinal image was optimized using the NIR-OCT, which was then turned off and the VIS-OCT was turned on to acquire a full 3D OCT dataset. The acquisition time was 1 second for an imaging volume containing 512×128 depth scans (A-scans).

Rhodopsin was then bleached by bright room light (~800 lx) for about 15 seconds, followed by acquisition of two light-adapted 3D images of the same retinal area. Each OCT cross-sectional image (B-scan) was manually segmented along the junction between the inner and outer segments (IS/OS) of the photoreceptors. An en-face view of the segmented OCT data was generated by summing the signal intensities from the IS/OS forward along the depth direction (FIGS. 4A-4E).

Figures 4A, 4B, 4C:
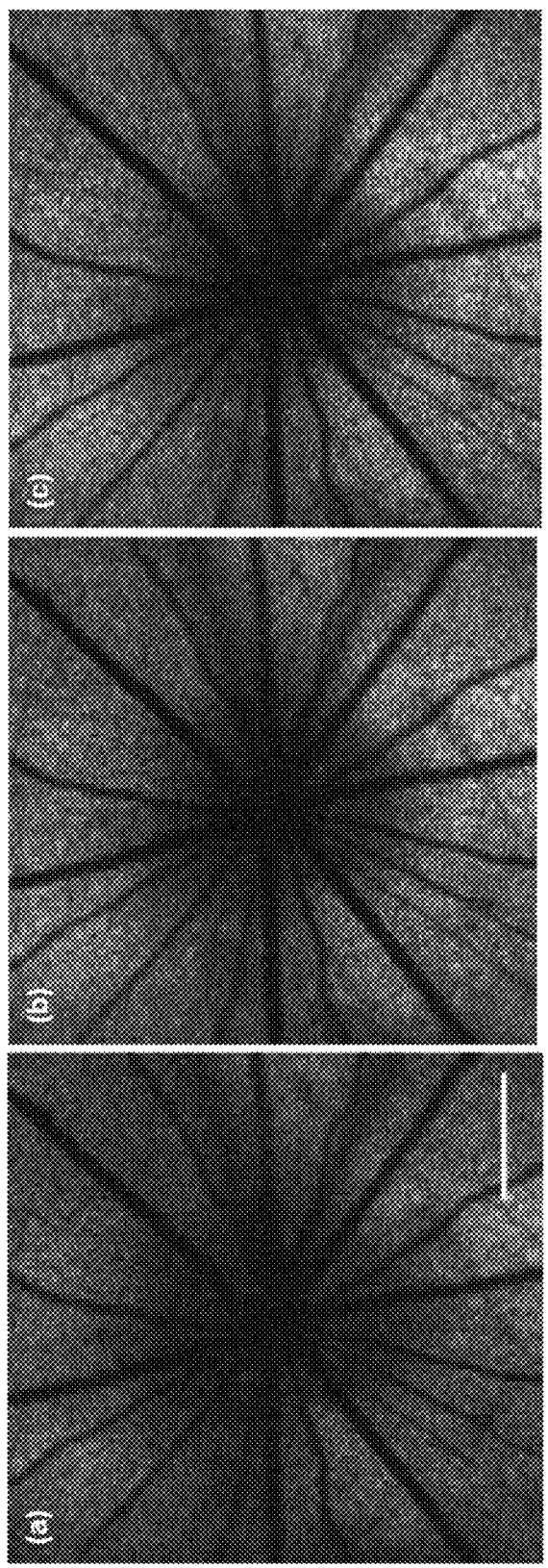
FIGS. 4A-4E are en-face representations of rhodopsin imaging of an albino rat retina displayed in the x-y plane. All the images were generated by summing the signal intensities from IS/OS forward along the z direction.
Figure 4D:
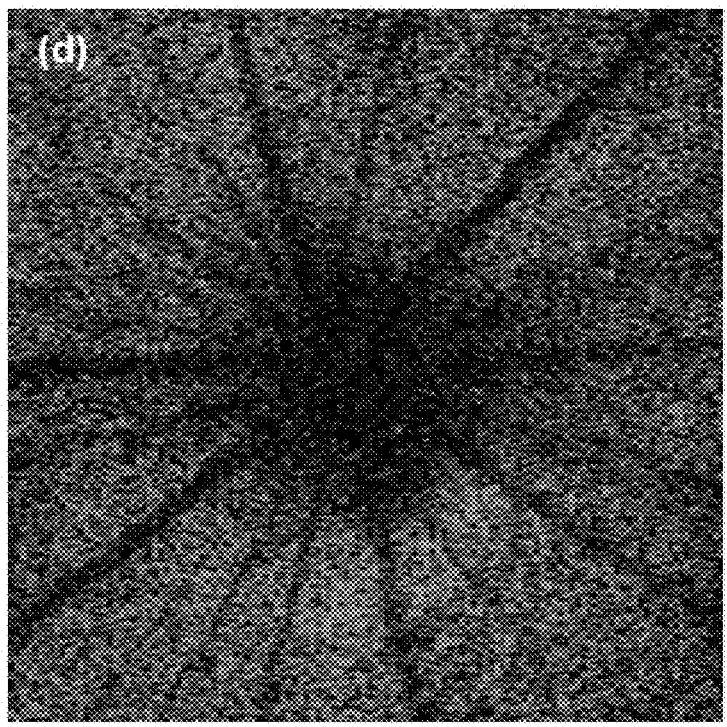
Figure 4E:
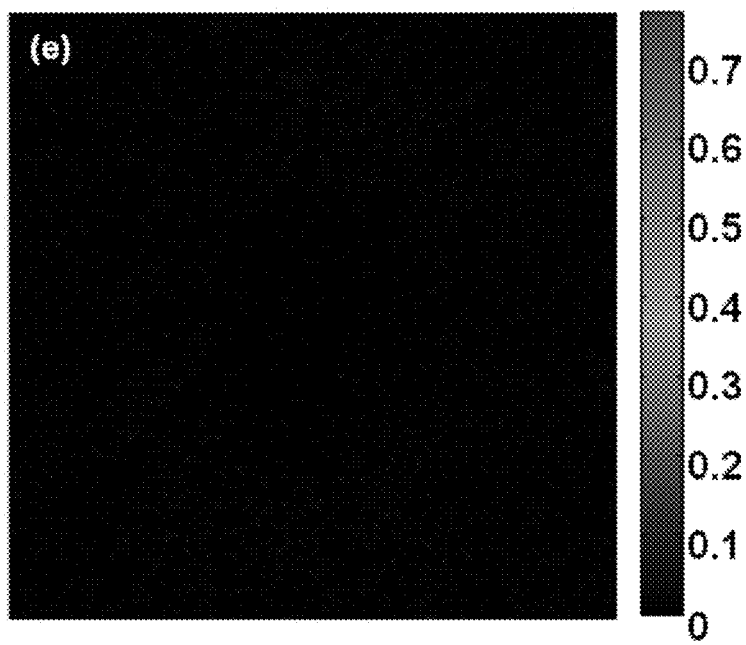

In most of the imaged area, the pixel intensities in the dark-adapted image were weaker than those of the same area in the two sequentially acquired light-adapted images (FIGS. 4B and 4C). This is clearly shown in the differential image (FIG. 2d) between the images of FIGS. 4A and 4B, calculated using Equation 2, where $I_{dark}$ and $I_{light}$ are the pixel intensity of the dark- and light-adapted images, respectively. The signals in FIG. 4D distributed evenly across the imaged area except at the optic disc where there were no photoreceptors. A differential image between the two light-adapted images (FIGS. 4B and 4C) was also obtained using Equation 2, substituting the pixel intensity of the first and second light-adapted image for $I_{dark}$ and $I_{light}$, respectively. The pixel intensities in the differential image between the two light-adapted images (FIG. 2E) are less than 5% of those in the differential image between the dark- and light-adapted images (FIG. 2D), indicating that the light reflection from the retina in the light-adapted states was stable. These results demonstrate the capabilities of the subject NIR/VIS-OCT apparatus in examining rhodopsin absorption.

The VIS-OCT approach with depth resolution also enables the segmentation of signals from the photoreceptor layer to construct the topographic rhodopsin distribution in the retina using the same 3D datasets of dark- and light-adapted retina in FIGS. 4A-4E.

Example 4

Figures 5A, 5B, 5C:
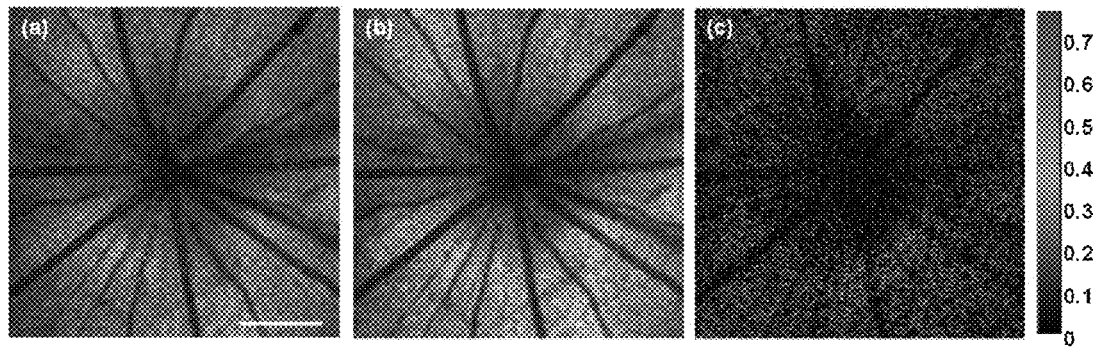
FIGS. 5A-5F illustrate the effect of segmentation on the contrast of rhodopsin imaging.
Figures 5D, 5E, 5F:
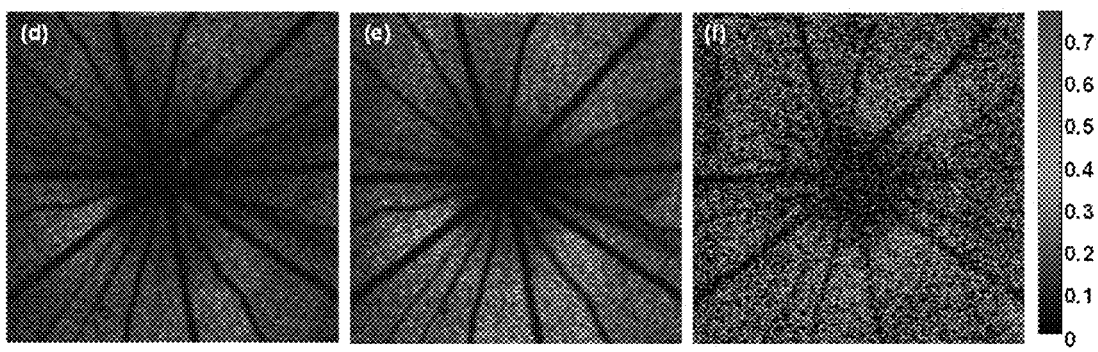

The depth resolution of OCT also provides experimental information of photon propagation in the retina, which is important not only in helping to accurately quantify rhodopsin concentration, but also in verifying theoretical fundus reflection models. The reflection from the sclera was previously included in the calculation of the theoretical model. The data provided herein, however, showed no sclera contribution although sclera is within the effective imaging range of the OCT system. Furthermore, the depth resolution enables the removal of the contribution from the choroid through segmentation, which simplifies the theoretical model. Segmentation would also make it more accurate to assess rhodopsin concentration regardless of the degree of pigmentation in the eye by removing signals from the choroid. Finally, with segmentation, the influence of reflection and attenuation of the probe light by tissues anterior to the photoreceptor layer on the quantification of rhodopsin can be eliminated. As a non-limiting illustration, comparison between the differential image calculated from reflections of the full-depth (FIG. 5C) and that of only the photoreceptor and the retinal pigment epithelium (RPE) layers (FIG. 5F) of the retina shows that the segmented image has better imaging contrast and is a more accurate representation of rhodopsin distribution in the retina.

Example 5

Figure 6A:
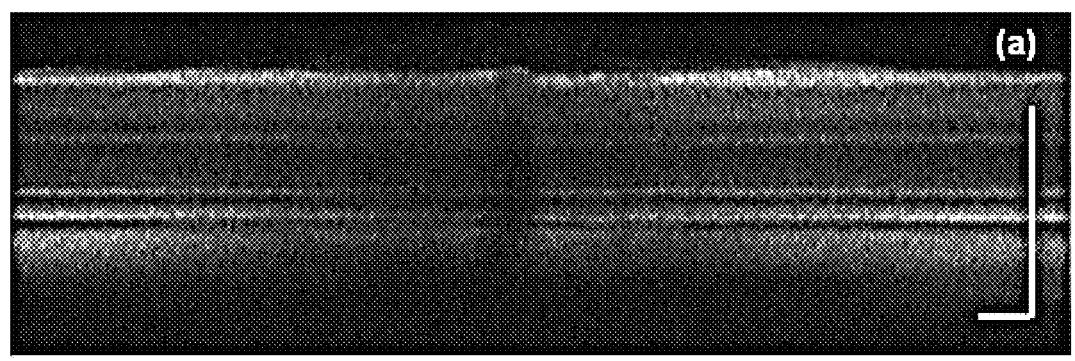
FIGS. 6A-6F illustrate the depth-resolved rhodopsin imaging of albino and pigmented rat retinas displayed in the x-z plane.
Figure 6B:
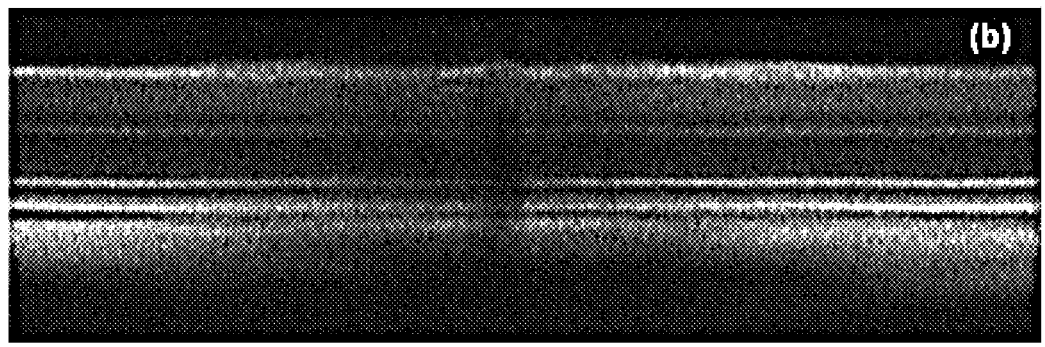
Figure 6C:
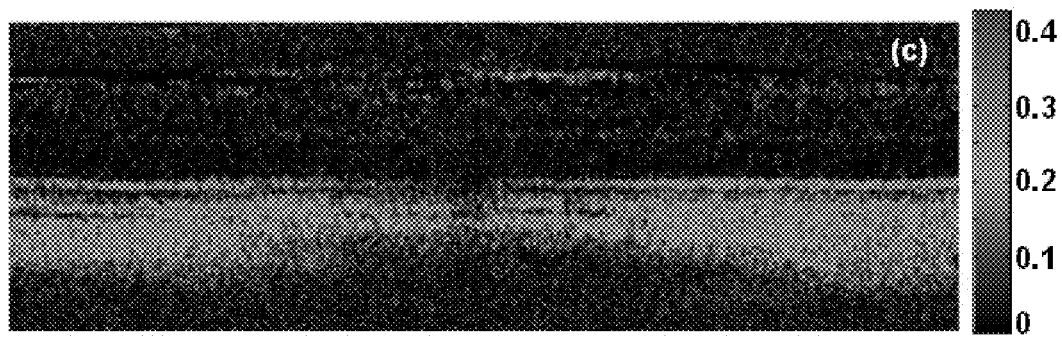

To investigate how the reflections from different retinal layers contribute to the differential image of FIG. 6C, each of the 128 OCT B-scans in the 3D datasets of dark- and light-adapted states was averaged to suppress speckle. Before averaging, the A-scans were shifted in each OCT B-scan image in the depth direction in reference to the IS/OS, so that the IS/OS became a straight line. All the rearranged B-scan images were then aligned also in reference to the IS/OS and averaged. FIGS. 6A and 6B show the averaged B-scan images in the dark- and light-adapted states, respectively. The calculation of the differential image was similar to that for the differential image between the dark- and the light-adapted images for a given B-scan in the x-y plane, except that the differential image in this case is projected in the x-z plane. The image (FIG. 6C) clearly shows that signals came from the layers corresponding to the photoreceptors, the retinal pigment epithelium (RPE), and the choroid. The residual high signal from some spots in the retinal nerve fiber layer (RNFL) is likely caused by slight misalignment between FIGS. 6A and 6B as well as insufficient speckle cancellation. The relatively weaker signal in the central region is caused by the optic disc, where photoreceptors are absent and the retina curves the most.

Figure 6D:
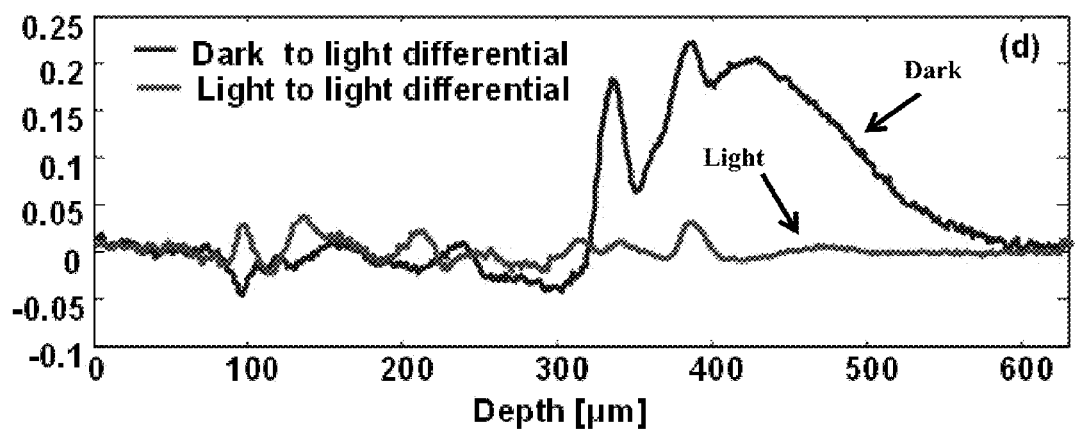

To further elucidate the changes in signals from different retinal layers between light- and dark-adapted states, the A-scans of FIG. 6C were averaged and presented in FIG. 3d (blue line). Peaks of absorption change are seen in the photoreceptor layer, the RPE layer, and the choroid. In comparison, the averaged A-scans of the differential image between the two sequentially acquired light-adapted OCT datasets (FIGS. 4B and 4C) showed no significant absorption changes (FIG. 6D, red line). The lowered signals from the retinal layers behind the photoreceptors in the dark-adapted state are also caused by rhodopsin absorption, similar to a shadowing effect caused by the photoreceptors. The probe light has to pass the photoreceptor layer to reach the RPE and choroid before being reflected. The reflected light again has to pass the photoreceptor layer before reaching the OCT interferometer. The light signals thus were attenuated by rhodopsin in either forward or return path.

Example 6

Figure 6E:
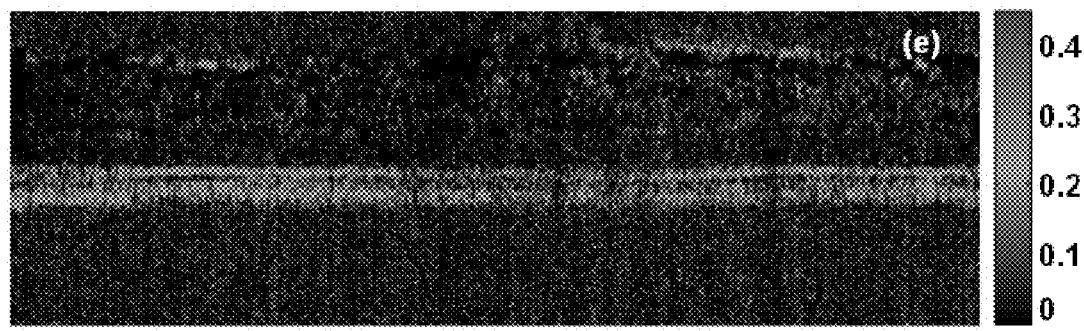
Figure 6F:
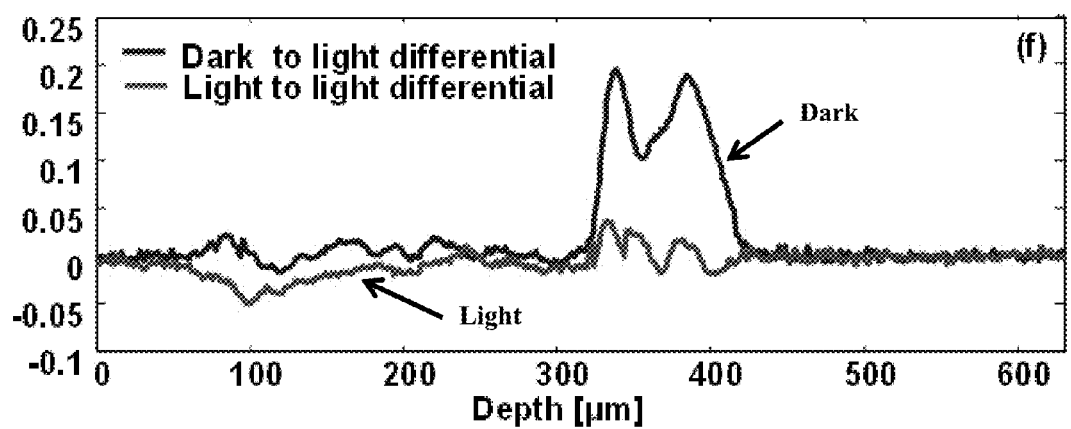

In pigmented animals, the RPE cells and the choroid contain light-absorbing melanin. To investigate how the presence of melanin in the RPE cells and choroid would affect light reflection, the retina of wild-type, pigmented Long Evans rat was imaged with the same procedure as for the albino rats. The depth-resolved differential image between the averaged OCT B-scans of the light and dark adapted states is shown in FIG. 6E, and the averaged A-scans of the differential image is shown in FIG. 6F. It is clear that in the pigmented animal, the photoreceptor layer and the RPE contribute to the difference of fundus reflections between the two states of adaptation. The contribution from the choroid seen in the albino animal is absent because of the strong optical absorption of melanin that absorbs both the incident and the scattered light. Thus, for pigmented animals, light reflected from behind the RPE can be neglected when quantifying rhodopsin from the measured fundus reflections.

Example 7

Figure 7A:
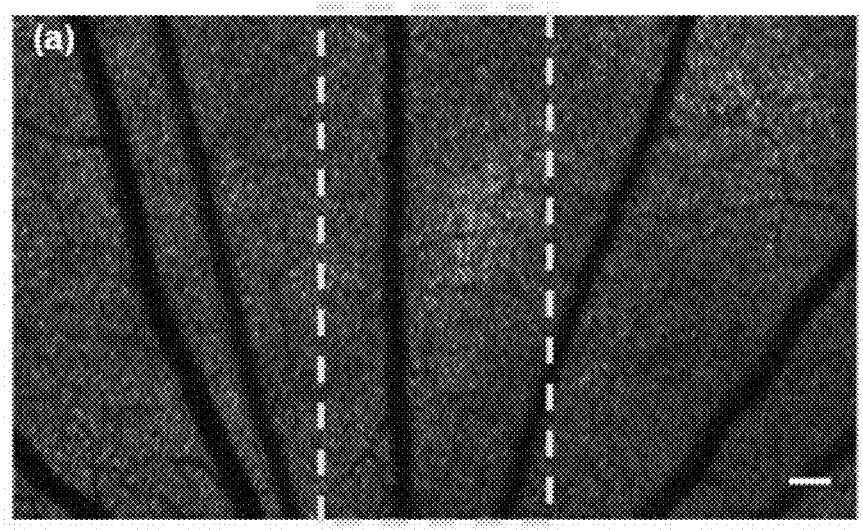
FIGS. 7A-7F illustrate rhodopsin imaging of albino rate retina following a patterned bleaching experiment.
Figure 7B:
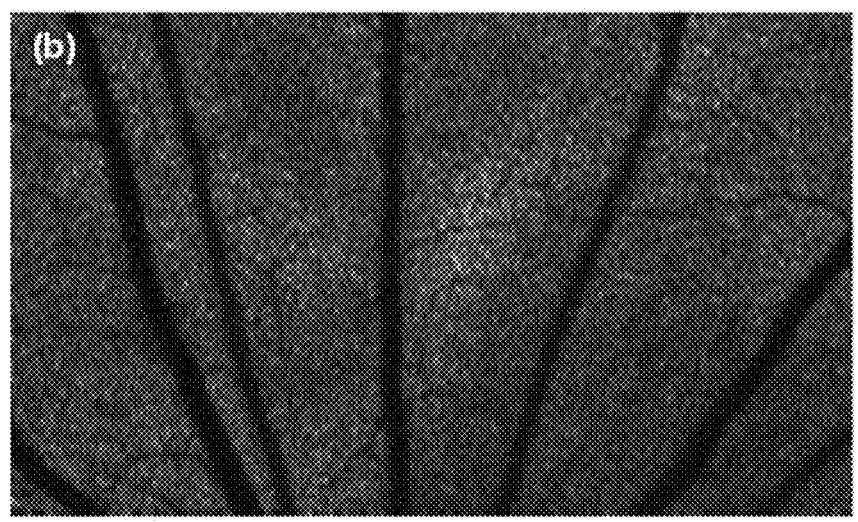
Figure 7C:
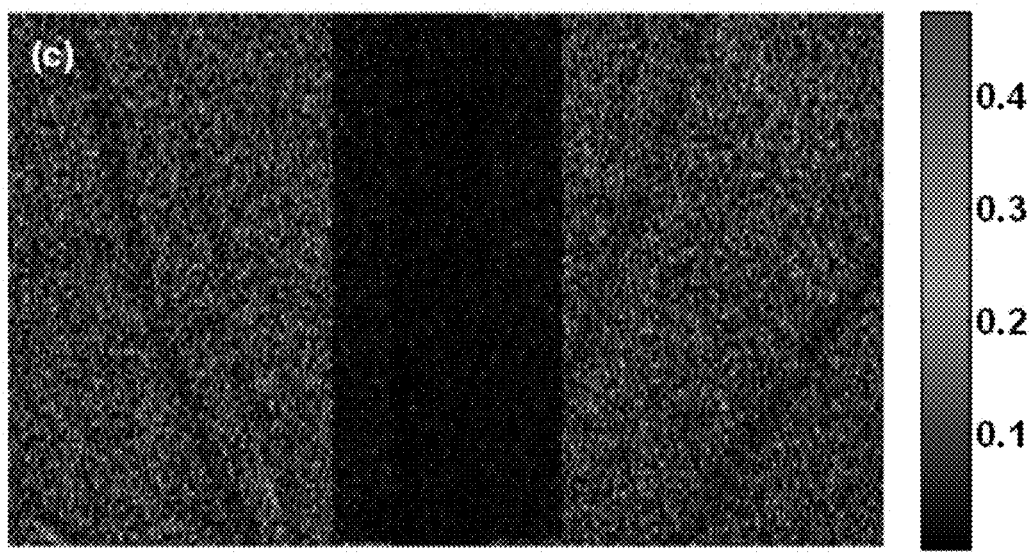
Figure 7D:
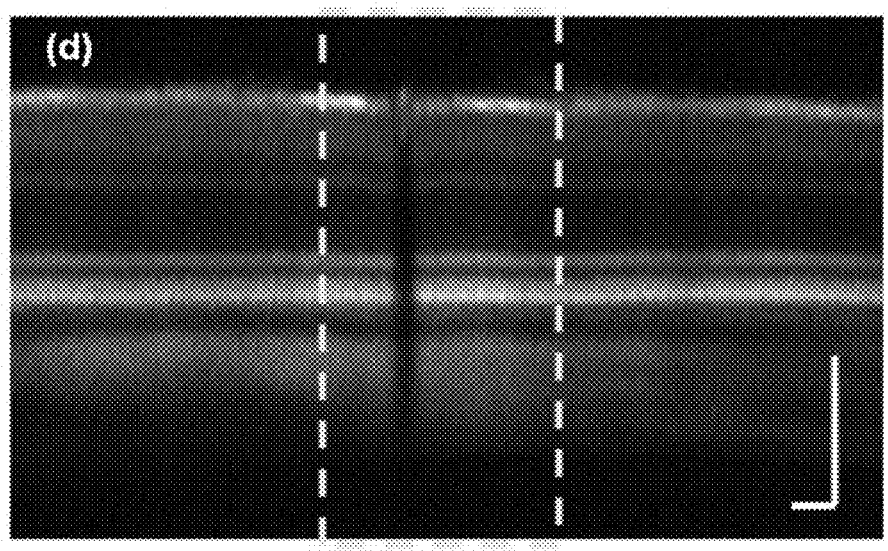
Figure 7E:
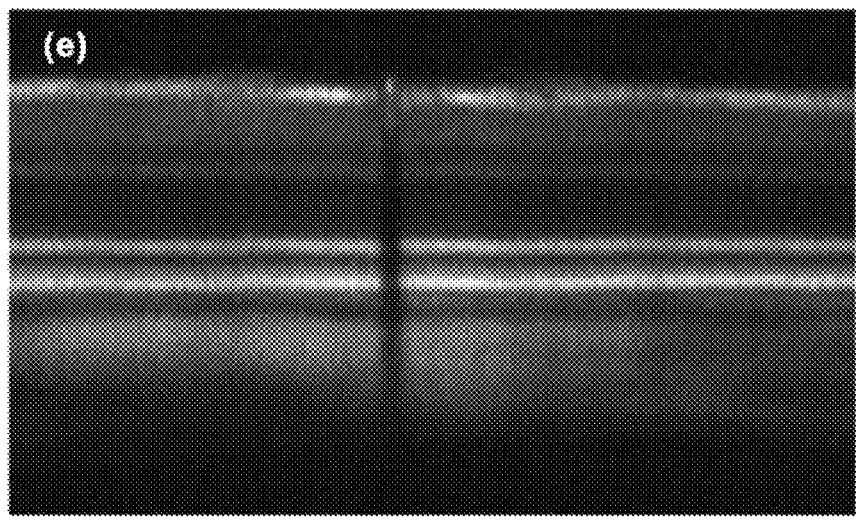

To further verify that the differential images provided herein represent the rhodopsin distribution, a patterned bleaching experiment was designed in which a vertical strip of retina 0.55 mm in width was pre-bleached by a total light energy of 160 nJ using a continuous-wave (CW) laser at 532 nm coupled into the optical fiber in the source arm of the OCT system. In this experiment, the animal was first dark-adapted and the retinal image was optimized by using the NIR-OCT. The vertical strip of the retina was bleached, followed by acquisition of a dark-adapted 3D VIS-OCT dataset (FIG. 7A shows the projection of the dataset on the x-y plane). Then, after about 15 s of light adaption, a second 3D VIS-OCT dataset was acquired. FIG. 7B shows the projection of the dataset on the x-y plane. The differential image (FIG. 7C), calculated with the same method as in FIG. 4D, clearly shows a vertical stripe of no absorption, which corresponds well to the pre-bleached pattern (area between the two yellow lines in FIG. 7A).

Figure 7F:
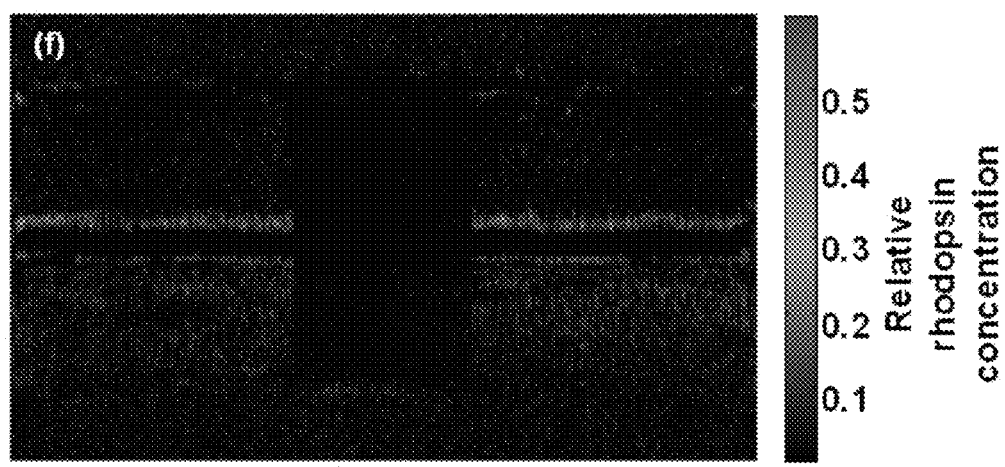

Another differential OCT B-scan image (FIG. 7F) was constructed using the same process as in FIG. 6C. A strip of retina with no absorption corresponding to the pre-bleached stripe is clearly seen in the photoreceptor layer, the RPE, and the choroid. Because rhodopsin in the photoreceptors is the only molecule bleachable at the wavelength and exposure level used, these results proved conclusively that the differential image represents rhodopsin distribution and the signals from the RPE and choroid in the differential image are also the results from rhodopsin absorption.

Example 8

An exemplary 8-channel SLO apparatus is described below. A parallel arrangement of 8 channels increases the imaging speed by a factor of 8 as compared to a conventional single-beam SLO imaging system. The laser source used herein has a pulse repetition rate (PRR) of about 100 kHz, which results in an imaging speed of 800 K-pixel/s. As a result, for an acquired image consisting of 256×256 pixels, the effect of eye movement during each frame of imaging is greatly reduced.

Figure 8A:
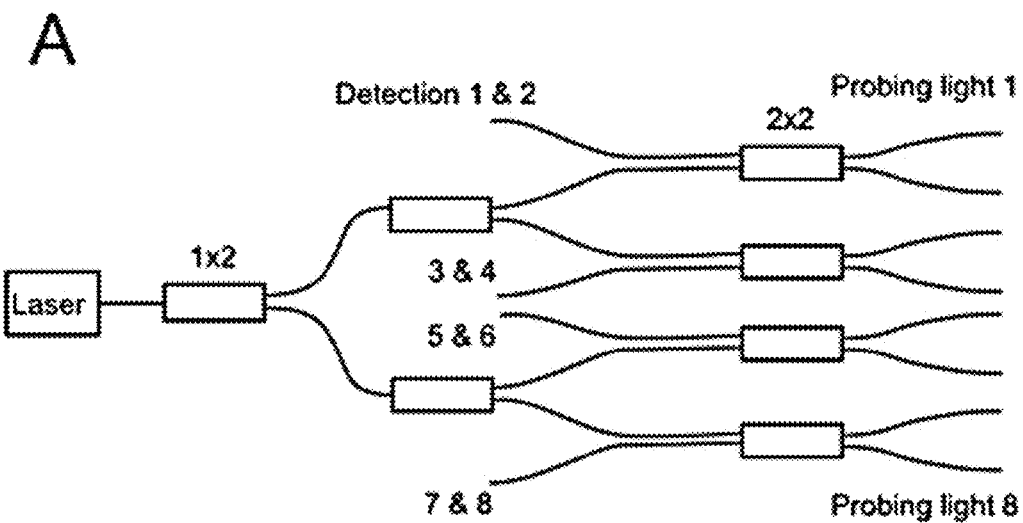
FIGS. 8A-8C illustrate the components of a modified SLO apparatus.

In this design, a light beam from a single light source of frequency-doubled Q-switched Nd:YAG laser (532 nm, 10 µJ/pulse, 2-ns pulse duration, and a maximal PRR of 30 kHz, SPOT-10-100-532, Elforlight Ltd, UK) is split into 8 beams by three-stage 1×2 single-mode fiber couplers connected in series. The two output ports of the primary coupler are then connected to two secondary 1×2 single-mode fiber couplers, each output port of which is once more connected to a tertiary 2×2 single-mode fiber coupler, resulting in a 1-to-8 split (FIG. 8A).

Figure 8B:
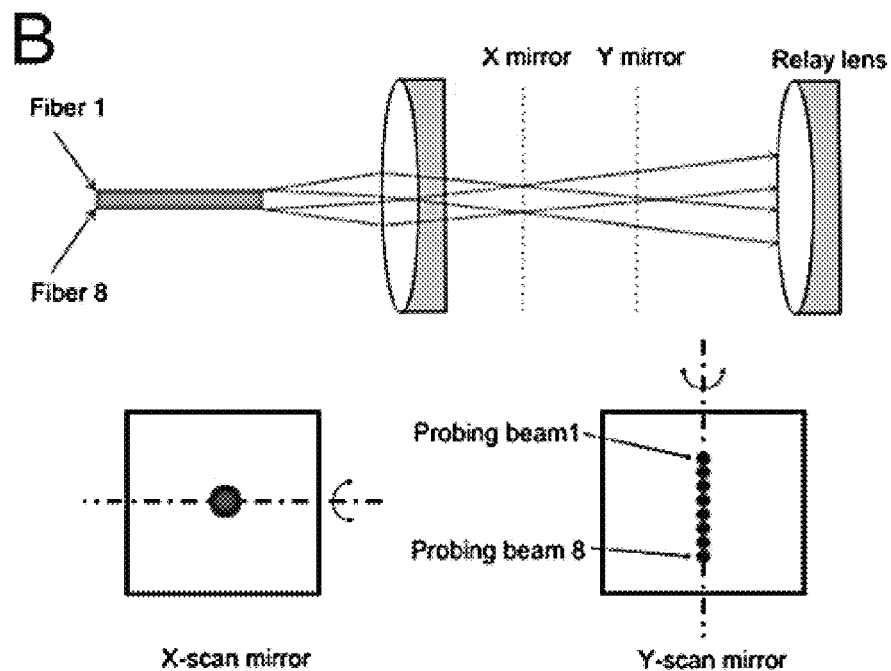
Figure 8C:
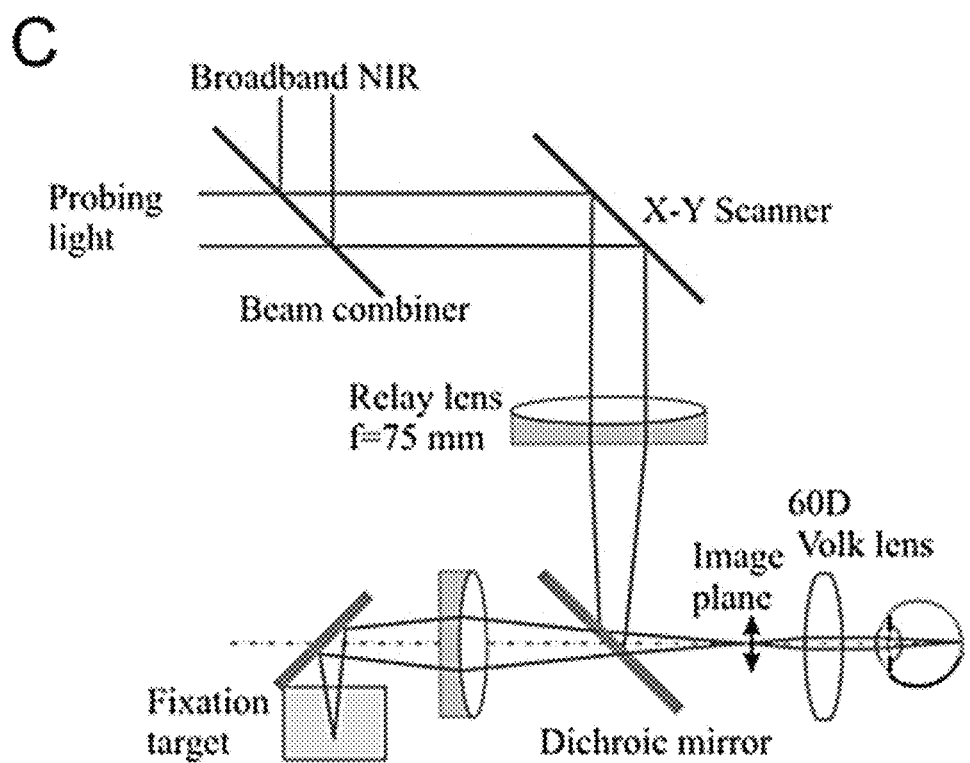

The 8 output fibers are aligned vertically and glued together with epoxy. The beams pass through a collimator (e.g., f=about 30 mm) and are scanned by the x- and y-mirrors of a galvanometer scanner. The x-mirror is placed at the pivotal point (the back focal plane of the collimator) of the collimated beams. FIG. 8B shows the positions of the probing beams on the two mirrors. A schematic of the arrangement of the optics is shown in FIG. 8C. This design allows 8 beams to be projected simultaneously onto the retina in a vertical configuration. The reflected signals from the 8 illuminated spots are collected by the ocular and relay lenses, de-scanned by the scanner, coupled back into each corresponding fiber, and detected by a single photomultiplier tube (PMT, e.g., H7422-40, Hamamatsu).

The cladding diameter of the fiber is about 125 µm. By putting 8 fibers in a row, the cross-sectional area of the fiber bundle is about 0.125×1 mm$^2$. The spread angle of the light beams across the retina is about 3.34° according to the parameters shown in FIG. 8C. The scanning data of the y-mirror are adjusted according to the different imaging angles required.

A 10-ns time delay is generated between two adjacent pulses in order to separate the reflected pulses from the 8 spots to achieve space-time coding. In this arrangement, the spatial information of detecting fibers 1-8 is coded by the order they are received by the PMT. At a given position on the scanner, the signal from fiber 1 is received first, followed by the signal from fiber 2 with a 10-ns delay, then signal from fiber 3 with another 10-ns delay, and so on. Since the spatial information is coded, the arrangement of the fibers at the detector side carries no spatial information and thus the fibers can be bundled into any configuration. When the fibers are bundled in a rectangular arrangement, e.g., 4×2 fibers, the cross-sectional area is about 0.50×0.25 mm$^2$, which is much smaller than the active area of the PMT and is unlikely to cause significant variance in the detection efficiency across the fibers.

Figure 9:
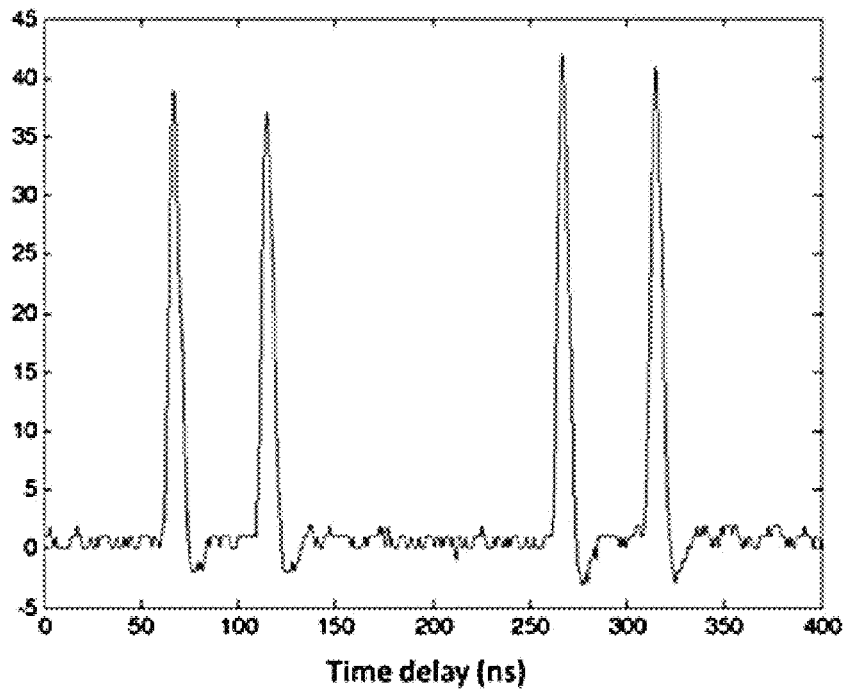
FIG. 9 shows the data for a time delay experiment of the SLO. The separation between the two pulses in each of the two-pulse trains is approximately 60 ns.

The 10-ns delay between two pulses is achieved by using optical fibers with different lengths. The time delay between pulse 1 and pulse 8 is about 70 ns, which requires a difference of 7 meters (round-trip) in length between the optic fibers, given a refractive index of about 1.5 of the core. The design of time delay was successfully tested in the experiment shown in FIG. 9 in which a 2×2 single-mode fiber coupler was used. The laser light was coupled into the input arm and was split into 2 by the two output arms. The length difference between the two arms was about 3 meters. Two mirrors were placed in contact with the ends of the two output fibers using a precision fiber positioning mount. The reflected light was detected at the detection arm with an avalanche photodiode. The separation of the two pulses in each of the two-pulse trains (FIG. 9) was about 60 ns.

Figure 10:
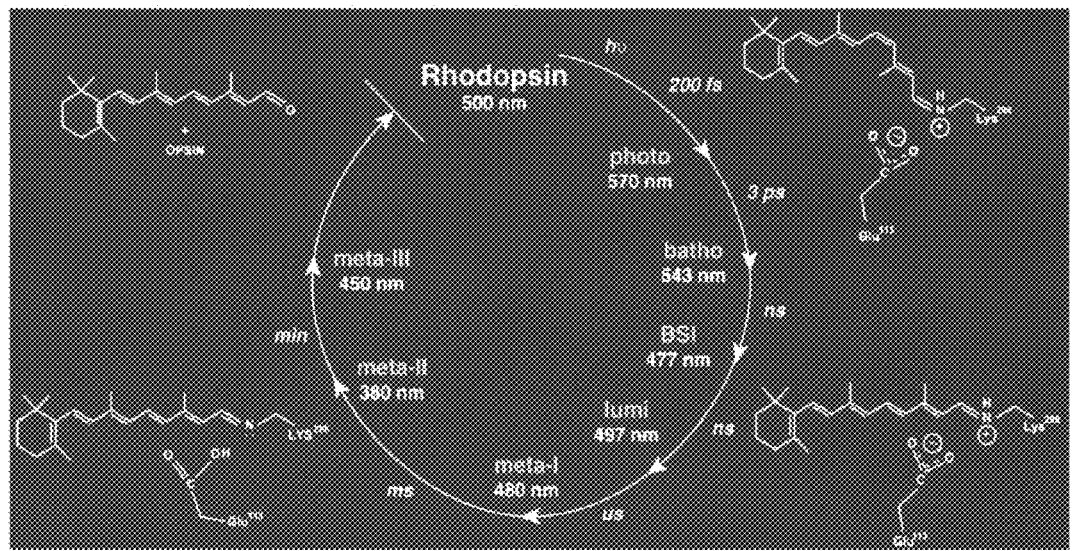
FIG. 10 is an illustration of the photocycle of rhodopsin. Upon light activation, a series of intermediates are generated. The absorption spectra of the intermediates in the first millisecond overlap the spectrum of rhodopsin.
Figure 11A:
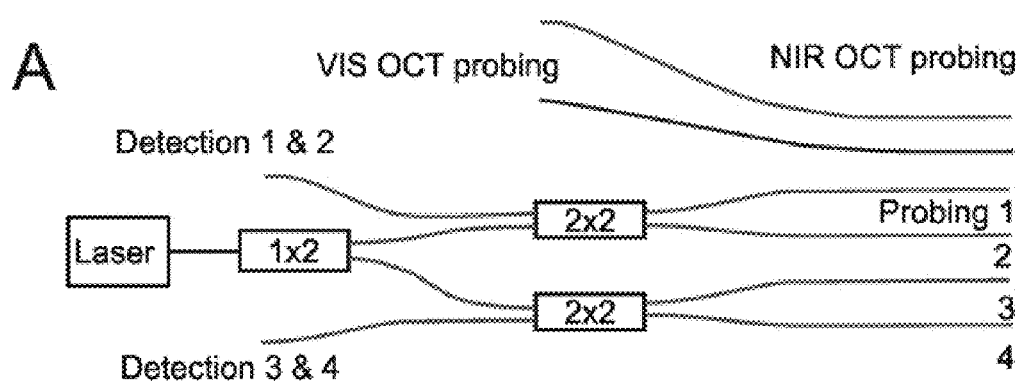
FIGS. 11A-11C represent a schematic of the integrated OCT-SLO apparatus.
Figure 11B:
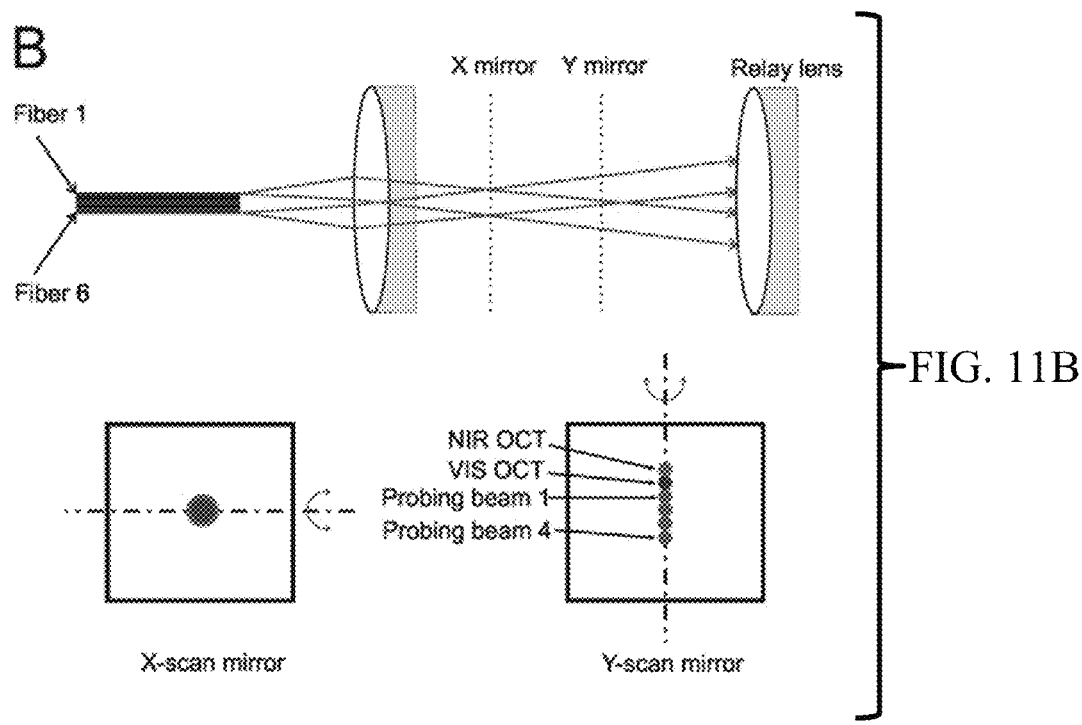
Figure 11C:
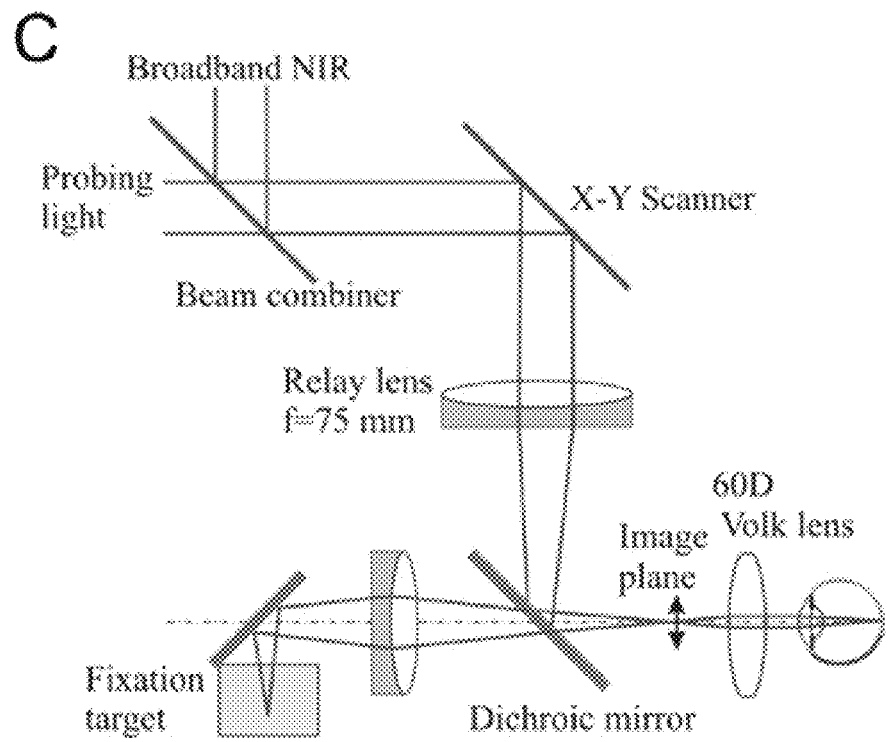

A nanosecond pulsed laser, such as the frequency-doubled Q-switched Nd:YAG laser, should significantly reduce the influence of absorption by rhodopsin intermediates, as indicated in FIG. 10.

In the integrated retinal imaging system, the set of optics, lenses, and scanner elements are commonly employed by both the OCT and the SLO, while the light sources and the detector are in accordance with each distinct apparatus.

Example 9

Figure 12A:
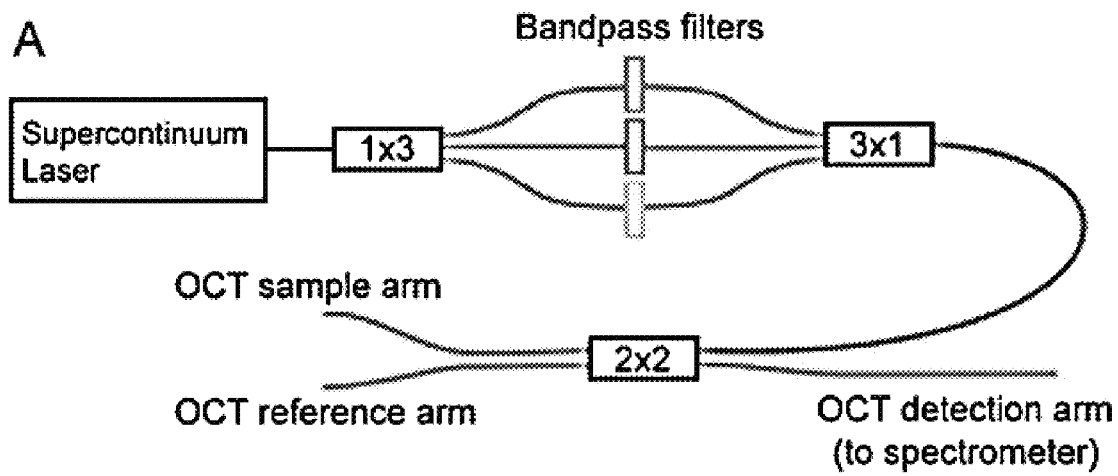
FIGS. 12A and 12B illustrate two designs for a triple-band NIR/VIS-OCT apparatus.
Figure 12B:
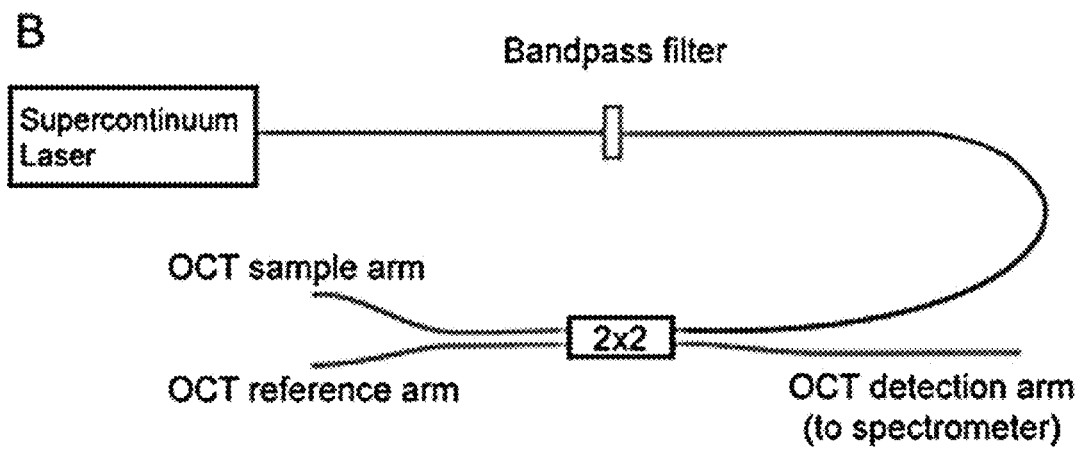
Figure 13:
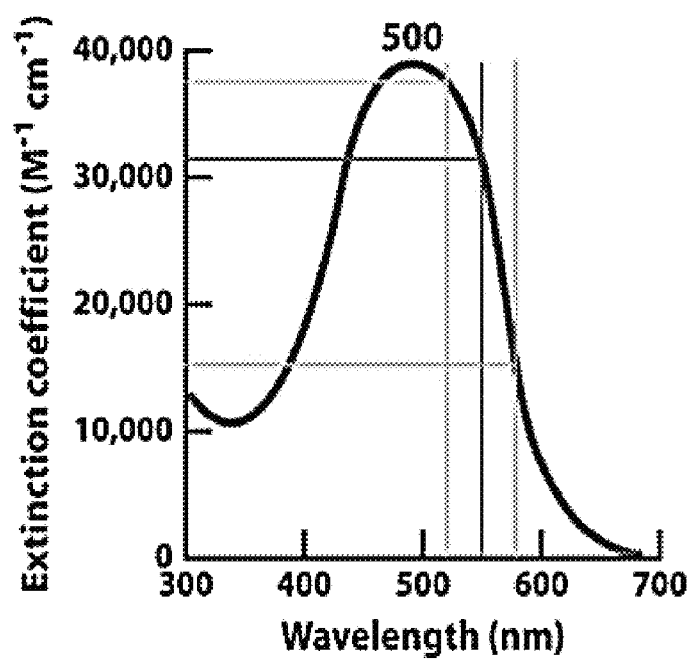
FIG. 13 demonstrates a rhodopsin absorption spectrum showing three wavelengths at 520 nm, 550 nm, and 580 nm, where distinct rhodopsin absorption coefficients exist, respectively.

Two different designs of a multiple-band NIR/VIS-OCT system are illustrated in FIGS. 12A and 12B. The first design (FIG. 12A) employs three separate band-pass filters. A broadband light source, for example, a supercontinuum laser (SuperK, NKT photonics), is split into 3 by a 1×3 single-mode optical fiber coupler, collimated, and passed through three band-pass filers with a center wavelength at about 520 nm, about 550 nm, and about 580 nm, respectively. Each band has a full width at half maximum (FWHM) of about 20 nm. The filtered light is coupled into a 3×1 fiber combiner to become a single beam. The combined light is then coupled into the source arm of a 2×2 fiber coupler to be split into the sample and reference arms of the OCT.

Figure 14:
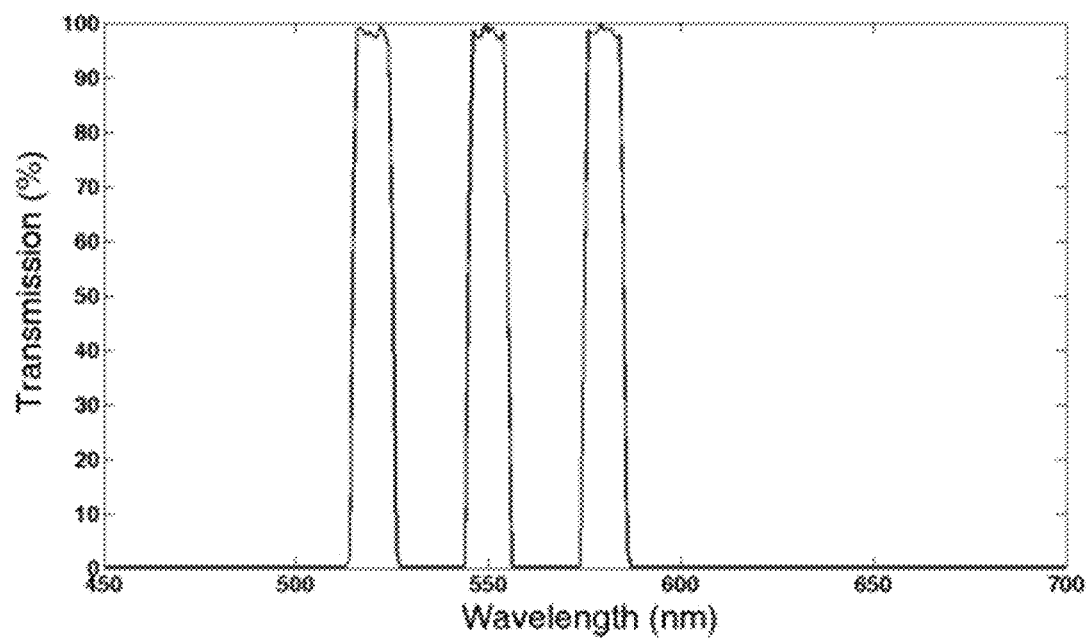
FIG. 14 shows the designed transmission curve according to each of the band wavelength of the triple-band filter.

The second design employs one customized triple-band filter through which the output light is filtered before being coupled to the source arm of a 2×2 fiber coupler (FIG. 12B). FIG. 14 shows the designed transmission curve of the filter provided by the manufacturer, which meets the specifications provided herein satisfactorily. The triple-band OCT has a line-scan CMOS/CCD camera built into the spectrometer operating at high line rate, for example, about 140 kHz. A single spectrometer will be used to detect all three bands of the OCT signals. For a line rate of about 140 kHz, the exposure time of the camera can be set at about 7 µs. The same clock is used to synchronize the camera and the galvanometer scanner. The rhodopsin exposure time is close to the camera exposure time (about 7 µs). With a total power of about 400 µW, the effective energy delivered to each spot is about 2.8 nJ, suggesting that about 10% of the rhodopsin are bleached at this exposure level. The triple-band VIS-OCT allows quantitative imaging of rhodopsin with dark adaptation only.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "consisting essentially of," as used herein, limits the scope of the ingredients and steps to the specified materials or steps and those that do not materially affect the basic and novel characteristic(s) of the present invention.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES 1. van de Kraats J, Berendschot T T, van Norren D. The pathways of light measured in fundus reflectometry. Vision research. 1996; 36(15):2229-47.
2. Morgan J I, Pugh E N, Jr. Scanning laser ophthalmoscope measurement of local fundus reflectance and autofluorescence changes arising from rhodopsin bleaching and regeneration. Investigative ophthalmology & visual science. 2013; 54(3):2048-59. PubMed Central PMCID: PMC3621503.
3. Berg J M, Tymoczko J L, Stryer L. Biochemistry. 7th ed. New York: W.H. Freeman; 2012.

What is claimed is:

1. An apparatus for evaluating the function of the retina of a subject based on an optical coherence tomography (OCT) technology, comprising a first source providing light in a near-infrared (NIR) wavelength, and a second broadband source providing light having wavelengths in a visible (VIS) spectrum; and the visible wavelengths being within the optical absorption spectrum of rhodopsin in the retina, the NIR light source is used for guiding the image alignment process before imaging with the VIS light source for rhodopsin absorption, and the apparatus further comprising an optical filter for separating the VIS light into a plurality of wavelength bands with center wavelengths in accordance with the wavelengths of distinct optical absorption coefficients characteristic to rhodopsin.

2. The apparatus according to claim 1, further comprising a scanning laser ophthalmoscope (SLO) integrated with the OCT apparatus.

3. The apparatus according to claim 2, wherein the SLO comprises a plurality of parallel optical fibers by which the laser source is split, the optical fibers illuminating pulsed laser spots onto the retina.

4. The apparatus according to claim 3, wherein the imaging speed of the SLO increases by a multiplication factor equivalent to the number of parallel optical fibers provided.

5. The apparatus according to claim 3, wherein the time delay between adjacent laser pulses is controlled by a difference in lengths between the optical fibers from which the pulses are delivered.

6. The apparatus according to claim 5, wherein the time delay between adjacent laser pulses is less than about 1 µs.

7. The apparatus according to claim 6, wherein the time delay between adjacent laser pulses allows the detection of the reflection of these pulses from the retina with a single detector.

8. The apparatus according to claim 1, the optical filter for separating the VIS light source into a plurality of wavelength bands comprising three distinct band-pass filters, or a single, three-band filter.

9. The apparatus according to claim 8, having three separate bands within the absorption spectrum of rhodopsin, and which is able to acquire three VIS-OCT images of the retina simultaneously.

10. The apparatus according to claim 1, the plurality of wavelength bands with center wavelengths being 520 nm, 550 nm, and 580 nm.

11. A method of examining the function of the retina of a human, comprising:
collecting three-dimensional images of the retina in a dark and a bright environment, respectively, using a visible-light optical coherence tomography (VIS-OCT) apparatus equipped with a visible (VIS) light source and a near-infrared (NIR) light source, the wavelength of the VIS light source being within the optical absorption spectrum of rhodospsin, and the NIR light source being used only for guiding the image alignment process before imaging with the VIS light source for rhodopsin absorption, and the VIS light source being separated by an optical filter into a plurality of wavelength bands with center wavelengths in accordance with the wavelengths of distinct optical absorption coefficients characteristic to rhodopsin;
quantifying the optical absorption of the retina in the dark and the bright environment, respectively, based on the intensity of the VIS-OCT images collected under each condition;
using an appropriate model of fundus reflection to correlate the difference in intensity of the images between the dark and the bright environments with the optical density of rhodopsin present in the retina; and
providing an assessment of the function of the retina based on the optical density of rhodopsin.

12. The method according to claim 11, wherein the method of using the VIS-OCT apparatus to collect three-dimensional retinal images comprises:
- allowing the subject to adapt to a dark environment;
- capturing a first series of cross-sectional images with the VIS light source in the dark environment;
- allowing the subject to adapt to a bright environment;
- capturing another series of cross-sectional images with the VIS light source in the bright environment; and
- reconstructing a three-dimensional differential image of the retina for the dark and the bright environment, respectively.

13. The method according to claim 12, wherein the three-dimensional retinal image comprises the spatial distribution of the rhodopsin whose optical absorption is quantified by the intensity of the images.

14. The method, according to claim 11, further comprising the use of a scanning laser ophthalmoscope (SLO) integrated with the VIS-OCT apparatus, and wherein, by utilizing a combination of the VIS-OCT and the SLO images, a quantification of the rhodopsin concentration is achieved such that the VIS-OCT image provides absorption information along a depth.

15. The method, according to claim 14, wherein quantitative rhodopsin distribution is calculated from three VIS-OCT images of dark-adapted retina simultaneously acquired, the three VIS-OCT images being in different wavelength bands determined by the optical filter used for separating the VIS light source.

* * * * *